US010888829B2

(12) United States Patent
Sarma et al.

(10) Patent No.: US 10,888,829 B2
(45) Date of Patent: Jan. 12, 2021

(54) PROCESS FOR SYNTHESIZING HYBRID CORE-SHELL MICROPARTICLES COMPRISING A POLYMER CORE AND A SILICON DIOXIDE SHELL WITH CONTROLLED STRUCTURE AND SURFACE

(71) Applicant: Bundesrepublik Deutschland, Vertreten Durch Den Bundesrepublik Für Wirtschaft Und Energie, Berlin (DE)

(72) Inventors: Dominik Sarma, Berlin (DE); Knut Rurack, Berlin (DE)

(73) Assignee: Bundesrepublik Deutschland, Vertreten Durch Den Bundesrepublik Für Wirtschaft Und Energie, Berlin (DE)

( * ) Notice: Subject to any disclaimer, the term of this patent is extended or adjusted under 35 U.S.C. 154(b) by 94 days.

(21) Appl. No.: 16/085,701

(22) PCT Filed: Mar. 17, 2017

(86) PCT No.: PCT/EP2017/056423
§ 371 (c)(1),
(2) Date: Sep. 17, 2018

(87) PCT Pub. No.: WO2017/158175
PCT Pub. Date: Sep. 21, 2017

(65) Prior Publication Data
US 2019/0091647 A1    Mar. 28, 2019

(30) Foreign Application Priority Data

Mar. 18, 2016 (DE) .................. 10 2016 105 122

(51) Int. Cl.
*B01J 13/14* (2006.01)
*B01J 13/00* (2006.01)
(Continued)

(52) U.S. Cl.
CPC ............... *B01J 13/14* (2013.01); *B01J 13/00* (2013.01); *B01J 13/0047* (2013.01); *B01J 13/20* (2013.01);
(Continued)

(58) Field of Classification Search
None
See application file for complete search history.

(56) References Cited

U.S. PATENT DOCUMENTS

| 6,103,379 A * | 8/2000 | Margel ............... B01J 13/14 |
| | | 427/212 |
| 6,479,146 B1 | 11/2002 | Caruso et al. |
| 2009/0017518 A1 * | 1/2009 | Wu ................. C12N 13/00 |
| | | 435/173.9 |

FOREIGN PATENT DOCUMENTS

| DE | 69612654 T2 | 11/2001 |
| DE | 10027744 A1 | 12/2001 |

(Continued)

OTHER PUBLICATIONS

Graf et al, "A General Method to Coat Colloidal Particles with Silica", American Chemical Society, vol. 19, pp. 6693-6700, (May 2003).

(Continued)

*Primary Examiner* — Jeffrey D Washville
(74) *Attorney, Agent, or Firm* — Bachman & LaPointe, PC

(57) ABSTRACT

Hybrid microparticle having a polymer core and a shell which surrounds the polymer core at least in sections and which has a silicon dioxide layer; characterized by an RF value, the RF value being defined as the ratio of an external surface area amenable to the adsorption of nitrogen to a surface area which is computable from an arithmetic mean diameter of the hybrid microparticle considered as an ideal sphere, where the shell has a structure selected from:

(Continued)

closed and smooth, with the shell having an RF value of between 1 and 1.5;
closed and hillocky, with the shell having an RF value of between 1.51 and 3; or
open, with the shell having an RF value of greater than 3.01.

21 Claims, 7 Drawing Sheets

(51) Int. Cl.
  *B01J 20/10*  (2006.01)
  *B01J 20/26*  (2006.01)
  *B01J 20/32*  (2006.01)
  *C08J 3/12*  (2006.01)
  *C08K 3/36*  (2006.01)
  *C09K 11/02*  (2006.01)
  *G01N 1/36*  (2006.01)
  *G01N 33/52*  (2006.01)
  *B01J 20/28*  (2006.01)
  *B01J 13/20*  (2006.01)
  *G01N 33/543*  (2006.01)
  *G01N 33/545*  (2006.01)

(52) U.S. Cl.
  CPC ............ *B01J 20/10* (2013.01); *B01J 20/103* (2013.01); *B01J 20/261* (2013.01); *B01J 20/264* (2013.01); *B01J 20/28019* (2013.01); *B01J 20/3291* (2013.01); *B01J 20/3295* (2013.01); *C08J 3/126* (2013.01); *C08J 3/128* (2013.01); *C08K 3/36* (2013.01); *C09K 11/025* (2013.01); *G01N 1/36* (2013.01); *G01N 33/52* (2013.01); *G01N 33/545* (2013.01); *G01N 33/5432* (2013.01); *C08J 2325/06* (2013.01); *C08J 2439/06* (2013.01); *C08L 2203/00* (2013.01); *C08L 2207/53* (2013.01); *G01N 2001/364* (2013.01)

(56) References Cited

FOREIGN PATENT DOCUMENTS

| DE | 69709668 T2 | 2/2004 |
| DE | 69724106 T2 | 6/2004 |
| JP | 06142491 A | 5/1994 |
| JP | 2009196829 A | 9/2009 |
| JP | 2009276431 A | 11/2009 |
| JP | 2010078767 A | 4/2010 |
| WO | 2004002225 A1 | 1/2004 |
| WO | 2011099932 A1 | 8/2011 |
| WO | 2014057976 A1 | 4/2014 |

OTHER PUBLICATIONS

Zou et al., "Polymer/Silica Nanocomposites: Preparation, Characterization, Properties, and Applications", American Chemical Society, vol. 108, pp. 3893-3957, (Aug. 2008).

Deng et al., "A Novel Method for the Fabrication of Monodisperse Hollow Silica Spheres", vol. 22, pp. 6403-6407, (May 2006).

Cao, "Preparation of silica encapsulated quantum dot encoded beads for multiplex assay and its properties", Analytical Biochemistry, 351, (2006), pp. 193-200.

Gorsd, "Polystyrene/silica microspheres with core/shell structure as support of tungstophosphoric acid", Materials Chemistry and Physics, 171, (2016), pp. 281-289.

International search report for patent application No. PCT/EP2017/056423 dated May 19, 2017.

Japanese office action for patent application No. 2019-500020 dated Oct. 25, 2019.

Chinese office action for patent application No. 2019-500020 dated Jun. 26, 2020.

Bamnolker, H.; B. Nitzan et al.: "New solid and hollow, magnetic and non-magnetic, organic-inorganic monodispersed hybrid microspheres: synthesis and characterization.", Journal of Materials Science Letters, vol. I6, No. 16, 1997,pp. 1412-1415.

Request for examination in Indian application No. 201847034894 dated Mar. 3, 2020.

Japanese decision to grant a patent for patent application No. 2019-500020 dated Oct. 29, 2020.

* cited by examiner ically, the product is always found as the decomposition of the particle. The yield of the particle. The yield of the particle. The yield of the particle.

PROCESS FOR SYNTHESIZING HYBRID CORE-SHELL MICROPARTICLES COMPRISING A POLYMER CORE AND A SILICON DIOXIDE SHELL WITH CONTROLLED STRUCTURE AND SURFACE

BACKGROUND OF THE INVENTION

The invention is situated within the field of the synthesis of microparticles for analytical use and as reference material, for example, in sensor technology, in medical diagnostics, and in research. The patent application relates more particularly to hybrid microparticles comprising a polymer core and a silicate shell, and also to hollow silicate spheres.

For particle-based analytical applications, there is a preference for using either spherical polymer particles or silicon dioxide particles. Suitable particles are in general a few micrometers in size, e.g. 5-7 μm (manufacturers: BD™ cytometric bead array or Luminex xMAP®) or 3 μm (manufacturer: Illumina) and have a substantially narrow size distribution (NIST monodispersity: typically 90% of the particles within 5% of the deviation of the median). From the standpoint of typical applications, a preferred size range is a mean particle diameter of about 0.5 μm to 10 μm. This range is dictated by the behavior, encompassing sedimentation and light scattering, of the particles typically dispersed in aqueous solutions in their use, and by the particular measurement method employed. Particles with a relatively low diameter of up to 500 nm are difficult to detect in imaging methods and methods based on scattered light; larger particles (greater than 10 μm) are increasingly subject to rapid sedimentation processes and are therefore unsuitable for fluidic high-throughput methods.

In the context used here, the expression "about", "around", and "substantially" denotes a deviation in the particular parameter from the stated value by not more than ±10%, typically by ±5%, and is therefore the same as a possible or actual fluctuation in the parameter in question that has no influence, or only a negligibly small influence, on a particular resultant technical effect of the parameter in question.

The range between 0.5 and 10 μm is preferred for particle-based applications. In this case it is always necessary to pay attention to the sedimentation of the particles, which is to be neither too slow, hence possibly leading to laborious separating and/or washing steps in the case of centrifugation, for example, nor too quick, so that during measurement on particle collectives or sequentially on individual particles (for example, characterization or application of the particles with scattered-light-based methods, high-throughput methods), the particles do not undergo sedimentation with time and so distort the measurement signal.

Spherical polymer particles, especially polystyrene particles, also referred to below as polymer core, can easily be produced in relatively large scales of up to several grams in the size range that is of interest, with a narrow size distribution in each case. Polymer particles, however, are of only limited amenability to subsequent chemical surface modification. In particular, their subsequent modification for chemical reactions of existing groups is restricted, meaning that functional groups that are needed in each case must already be present in the form of comonomers in the reaction mixture used for the particle synthesis. Likewise, polystyrene particles are distinguished by a low physical density of about 1.05 g/ml, and so, while being colloidally stable in aqueous solution, nevertheless require either long times or very high rotational speeds for separation by means of centrifugation, for example. Usually, therefore, polystyrene particles are used in relatively large diameters of greater than 3 μm.

In contrast to this, silicon dioxide particles, referred to hereinafter as silicate microparticles, can easily be subsequently functionalized by means of organic chlorosilane derivatives or alkoxysilane derivatives. On account of the high physical density of about 2.0±0.2 g/ml, however, they undergo rapid sedimentation in aqueous media. Furthermore, the synthesis of silicate microparticles beyond the classic "Stöber range", i.e., with a mean particle diameter of greater than 1 μm, necessitates multistage methods which are costly and inconvenient.

A further physical property which is important from the application standpoint is the light scattering by the individual particle, as determined authoritatively via the refractive index. In scattered-light-based methods, efficient light scattering is an important requirement. In this regard, polymer particles, such as polystyrene particles, for example, are notable for a suitably high refractive index of n=1.59 (for an excitation wavelength of 589 nm), whereas silicate microparticles display a lower value of n=1.46 (for an excitation wavelength of 589 nm). For a given size and excitation wavelength, this results in low scattered-light intensity of individual silicate microparticles, in flow cytometry, for example, by comparison with polystyrene microparticles.

In optical applications, the particles obtained preferably have a scattered-light intensity which at least corresponds to that of the polystyrene core or lies above it. Similarly, a refractive index is assumed that corresponds at least to that of pure polystyrene cores. In accordance with the preferred use of the particles in particle-based analytical applications, the scattered-light intensity is determined on the basis of the forward scattering at 180°, abbreviated FSC, and of an excitation wavelength of 488 nm, by flow cytometry, with the pure polymer core being used as a reference.

A further physical property important from the application standpoint is control over the structure and associated surface area of the spherical supports. Commercial solutions at present pay no account to this aspect, having preferably operated here to date with pure polymer microparticles and/or silicate microparticles. With regard to their structure, these microparticles are always treated as ideal spheres with a smooth surface. This disregards the possibility of increasing the surface area per particle or placing structure-reactivity relationships in the foreground.

SUMMARY OF THE INVENTION

Against this background, there is a need for ideally monodisperse, spherical microparticles in a size range of between 0.5 and 10.0 μm with a silicatic surface that have adequately efficiently light scattering and suitable sedimentation properties, determinable via an adjustable density of between $\rho=1.05$ g/cm$^3$ and $\rho=1.8$ g/cm$^3$, preferably between $\rho=1.09$ and $\rho=1.53$ g/cm$^3$, in aqueous solutions. As a practicable approach to the preparation of suitable microparticles, the approach pursued here is the synthesis of hybrid core-shell particles, with a shell of silicon dioxide being applied with a controlled structure to spherical polymer cores with a narrow size distribution. Particles of these kinds are referred to here as hybrid microparticles. The density of such particles is computed from the sum total of the mass fraction of the polymer core times the density ($\rho=1.05$ g/cm$^3$) and from the mass fraction of the silicate shell times the density ($\rho=2.00$ g/cm$^3$). The mass fraction of polystyrene or silicate, respectively, in a hybrid particle assembly can be determined by means of thermogravimetric analysis. The fractions of the silicate shell within the density of the hybrid microparticles are preferably here between 5% and 50%. The resulting densities of the hybrid microparticles are therefore between around $$1.098 \frac{g}{cm^3} = 0.950 * 1.050 \frac{g}{cm^3} + 0.050 * 2.000 \frac{g}{cm^3} \text{ and}$$
$$1.525 \frac{g}{cm^3} = 0.500 * 1.050 \frac{g}{cm^3} + 0.050 * 2.000 \frac{g}{cm^3}.$$

Proposed against this background are hybrid microparticles, a method for producing such microparticles, the use of 4,4'-azobis(4-cyanopentanoic acid) as initiator for a radical polymerization, a chromatographic support, and a support particle for a particle-based assay all as disclosed herein. Further embodiments, modifications and improvements will become apparent from the description and figures hereinafter and also from the appended claims.

According to a first embodiment, microparticles are proposed which comprise a polymer core and a shell which surrounds the polymer core at least in sections and which comprises a silicon dioxide layer. These hybrid microparticles are characterized in accordance with the invention on the basis of the ratio of the specific outer surface area amenable to adsorption of nitrogen, and therefore determinable by means of commonplace methods via an isotherm, to the surface area computable from an arithmetic mean diameter of the hybrid microparticles on assumption of an ideal spherical form thereof. This ratio of specific surface area determined by nitrogen adsorption to the surface area computed from an arithmetic mean particle diameter for the hybrid microparticle considered as an ideal sphere is referred to below as the roughness factor or RF value.

The external surface area is determined preferably by nitrogen adsorption, on the basis of the possibility of using a BET isotherm for describing the adsorption and desorption events of nitrogen at 77K, or alternatively is estimated from the number of silicate nanoparticles encompassing the silicate shell and the bulging thereof in the case of closed shells or the size and number thereof in the case of open silicate shells.

In the absence of any data on the nitrogen adsorption of the particles, the external surface area value for open shells is calculated from the core size and from the size and number of the silicate nanoparticles encompassing the silicon dioxide layer: number of particles times their surface area, determinable via the size on the assumption of an ideal sphere. The number of silicate nanoparticles is calculated in turn by the mass fraction of silicate in the hybrid particle assembly, determinable by means of thermogravimetric analysis (TGA), on the assumption of a mean density of about 2.0 g/ml. For closed particles for which there are no nitrogen adsorption data, the RF value is estimated from electron micrographs of the particles. In the case of closed shells (smooth or hillocky), the mean bulging of the silicate nanoparticles encompassing the silica shell and predominantly fused with one another is respectively assessed, and their surface area is calculated. This produces theoretically possible RF values of between 1 and 2, on the assumption of silicate nanoparticles which have bulged up to a maximum of half of their diameter. The size of the silicate nanoparticles is not relevant here, since it is only the bulging that determines the growth of the surface area. In real situations, RF values obtained for hillocky hybrid microparticles are in some cases between 2 and 3. This is generated by additional silicate nanoparticles, bulged in some cases beyond their mean particle radius, which adhere to the silicate shell and/or have fused with it.

Advantages of this embodiment arise from the fact that, by way of the PVP-adjustable structure and hence specific surface area of the silicate shell, it is possible to achieve an adjustable occupation density per particle with functional groups or with ligands and/or fluorophores. Furthermore, via the structure and thickness of the silicate shell, it is possible to adjust a resultant density of between 1.05 and 1.8 g/cm³, preferably between 1.09 and 1.53 g/cm³, for the hybrid microparticles. Moreover, as an initiator for the radical polymerization of the polymer cores, it has been common to date to use AIBN ((2,2'-azobisisobutyronitrile), which is environmentally damaging (H412) and toxic (H302, H332). With AIBN, furthermore, it is difficult to produce particles of narrow size distribution using PVP with an average molecular weight of less than 25 000 daltons, since the non-polar initiator does not generate sufficient charges on the surface to stabilize the particle during the synthesis.

The embodiment proposed is further characterized in that the surface structure of the shell is selected from: smooth—in which case the RF value is between 1 and 1.5; hillocky—in which case the RF value of the shell is between 1.51 and 3; or open—in which case the hybrid structure has a roughness factor of above 3.01.

Advantages of these characterizing features emerge from the fact that the surface area of the hybrid microparticles and their RF value can be adjusted through the polymers used in their production. Hence in comparison to an ideal sphere, in the case of smooth shells and RF values of 1 to 1.5, corresponding surface area increments of up to 50% are possible; in the case of hillocky shells with RF values of between 1.51 and 3.0, increments of up to 200% are achievable; and in the case of riven shells with RF values above 3.01, increments of well above 200% are achievable.

According to a further embodiment, the structure of the shell is further selected from:
open, with the shell-comprising pores having a pore diameter of above 50 nm (macropores) and/or below 50 nm (mesopores and micropores), and
closed, with the native silicate shell having no pores, more particularly no micropores (diameter less than 2 nm), no mesopores (diameter of between 2 and 50 nm), and no macropores (diameter greater than 50 nm).

The presence of pores here, on the one hand, is concluded on the basis of a visual assessment of scanning electron micrographs of the particles (mesopores and macropores) or alternatively (preferably) is judged on the basis of curve fitting of the adsorption in accordance with a BET isotherm and the resultant C value (micropores), or the describability of the desorption profile of nitrogen (mesopores) on a particle sample.

The "less than 2 nm" statement has no lower limit, with the possible consequence of sub-nanometer-sized pores in the shell. Alternatively, in accordance with the invention, the C value is used as a basis for dimensioning, and in this case the range is also expanded to C less than 200, thereby not ruling out the minimum presence of micropores, meaning that the shells thus designated may indeed also encompass micropores. The use of the C value, which is described in more detail later on, appears to be suitable for giving an indirect description of the porosity actually present in the silicate shell.

Advantages of this embodiment emerge from the fact that the shell structure leads to different steric shielding, the surface of closed shells (with RF values of between 1 and 3) therefore being more accessible for larger molecules (greater than 1 nm) such as, for example biomolecules (DNA, proteins or other biopolymers), whereas in the case of open shells (RF values greater than 3.01) the entire surface area is not available for covalent or adsorptive bonding of large molecules. Smaller molecules, on the other hand, are readily able to bind to open shells, thus enabling in this case a particularly high density of bound small molecules per particle.

According to a further embodiment, the polymer core of the microparticle comprises a polymer component which is selected from polystyrene, a polystyrene derivative and/or a comonomer. The molecules of the selected polymer component each have at least one polymerizable double bond, and so the polymer core may consist either of alternating copolymers, block copolymers, or of a mixture of polymer and copolymer.

Advantages of this embodiment arise from the fact that, for example, dyes which possess a double bond, organic or inorganic nanoparticles which are functionalized with a polymerizable double bond, or other comonomers can be incorporated into the core in order to determine the functionality (color, fluorescence, degree of crosslinking, Raman coding by different styrene derivatives) of the polymer core.

According to a further embodiment, the polymer core of the microparticle is furnished with a polyvinylpyrrolidone (hereinafter also abbreviated as PVP), the PVP having an average molecular weight in the range from 7000 daltons to 360 000 daltons.

Advantages of this embodiment emerge from the fact that by means of the PVP it is possible to carry out targeted adjustment of the specific surface area and/or the structure of the silicate shell of the hybrid microparticles. An advantage is that PVP is commercially available commercially in a grade which is standardized in terms of its molecular weight (e.g. Kollidon or Luviskol, BASF) or (PVP 10, PVP40, PVP K-60 or PVP360 CAS: 9003-39-8, Sigma Aldrich).

According to a further embodiment, the PVP is covalently bonded on an outer surface of the polymer core, since crosslinking of the PVP chains with the polystyrene oligomers that form during the core polymerization can be assumed.

Advantages of this embodiment include an increased stability of the particles during and after the polymerization, in washing steps, for example, and the possibility of growing a silicate shell onto the polymer core subsequent to the synthesis, without having to modify the core otherwise.

According to a further embodiment, the hybrid microparticles described here in native form, in other words as they are preparable by means of the wet-chemical synthesis described in detail hereinafter, comprise a layer of PVP which is on the core and in the case of P1 is below the silicon dioxide shell, in the case of P2 is partly incorporated into the shell, and in the case of P3 is within the mesopores and/or macropores of the shell. This is determined in particular on the basis of the prevailing forces which are responsible for the formation of the silicate shell on the polymer core. For instance, at molecular weights below 25 000 Da, the silicate shell is formed directly on the core particle principally by electrostatic and acid-base interactions between the silicate nanoparticles and silica intermediates, which occur during the coating operation, and the carboxylic acid, which are present on the surface as a result of the initiator. In contrast, in the case of a molecular weight of more than 58 000 Da for the PVP, the primary assumption is of the adsorption of silicate nanoparticles on the PVP chains, since the carboxylic acids are shielded by the longer PVP chains. For PVP with a molecular weight of between 25 000 Da and 58 000 Da, mixed forces can be assumed. In the case of longer PVP chain lengths, more adsorption sites are provided outside the core surface, at which silicate nanoparticles are able to attach, in order to form an open structure. Consequently in the case of closed, smooth shells the PVP chains are beneath the silicate shell; in the case of closed, hillocky shells they are partly within the shell; and in the case of open shells, they are between the silicate nanoparticles.

Advantages of this embodiment encompass the possibility that in the case of P1 there is an increased stability of the shell with respect to thermal energy, because the closed shell protects the inner polymer core. When the core undergoes decomposition, the shell would ultimately break, allowing composition products to escape. This can be shown by means of thermogravimetric analysis, since in that case a large part of the polymer core burns only at a temperature of greater than 500° C. (cf. FIG. 2).

In accordance with the practical working example P2, in contrast, during a thermal treatment of between 50 and 200° C., preferably at 80-120° C., over a period of, for example, 5 hours, the PVP chains can be displaced from the shell and therefore micropores can be generated for functionalization within the shell. At the same time, in analogy to the practical working example P3, in which mesopores are present from the outset, an unhindered thermal decomposition of the core can be brought about at temperatures above 200° C., and so the hollow silicate spheres subsequently present (cf. FIG. 5) are intact.

According to another embodiment, the PVP, bonded covalently on the polymer core on the one hand, at the same time has a non-covalent bond to the shell, via hydrogen bonds between the carbonyl group of the PVP and the silanol groups of the silicate shell, with the shell comprising silicon dioxide, more particular a multiplicity of silicate nanoparticles bridged with one another covalently via Si—O—Si bonds. In delimitation of the structures obtained, the assumption here is of a predominantly fused structure of the silicate nanoparticles in the case of P1 and P2. Accordingly there is no layer of accreted silicate nanoparticles, forming an open shell structure; instead there is a closed shell structure with roughness factors of between 1.0 and 1.5, or between 1.51 and 3. Silicate nanoparticles present in a loose assembly, as described for example in U.S. Pat. No. 6,103, 379 A or 6,479,146 B1, which resemble the structure obtained in working example P3 (analogously to the PVP used with 360 000 daltons in the case of U.S. Pat. No. 6,103,379 A), result in roughness factors of greater than 3.01. For the determination of the roughness factors, the external surface area is calculated by the number of silicate nanoparticles times their surface area, determined via the average size and the assumption of an ideal sphere. The number of silicate nanoparticles can be determined in turn via the mass fraction (ascertained by thermogravimetric analysis) of the silicate shell in the hybrid particle assembly, taking account of an average density of 2.0 g/ml and an average size of the silicate nanoparticles. Hence the roughness factors according to U.S. Pat. No. 6,103,379 A are 3.66, 5.92 and 8.15, analogously to the TGA values found of 7.8%, 13.5% and 18.5%, for a core size of 1.8 μm and an average silicate nanoparticle size of 30 nm.

Surprisingly it turned out that the thickness of the silicate shell can be controlled authoritatively by the choice of the PVP. Hence the shells are between 10 and 30 nm thick in the case of microparticles according to working example P1, between 30 and 45 nm in the case of P2, and between 40 and 70 nm thick in the case of P3. The ratio selected in each case here for the volume of TEOS used to the mass of the polymer cores used is 3:1, as for example 3 ml of TEOS to 1 g of core particles used. Furthermore, there is no longer any authoritative change in the thickness or in the structure. Amounts of TEOS up to a ratio of 9:1 were tested here in steps. Below that, in other words for example, at a ratio of 1:2 or 1:1, smaller silicate nanoparticles are in each case able to attach in single layers (monolayers) so as to form open structures even at relatively low PVP chain lengths. From the standpoint of the applications mentioned at the outset for the hybrid microparticles, closed shells are desirable, since open shells are occasionally not very stable; silicate nanoparticles may fall off, for example, and—as described here and also elsewhere—relatively poor analytical signals are obtained in the case of larger biomolecules. From the standpoint of an analytical application in particle-based assays, the benefit from a gain in surface area outweighs the above-stated disadvantages possibly only in the case of particles according to P3, especially if smaller molecules are preferable for attachment to the hybrid microparticles, or relatively small analytes are being tested in the assay.

Advantages of this embodiment emerge from the fact that the production method is highly reproducible if a minimum amount of TEOS of 3:1 is used, since the shell thickness and structure no longer undergo any authoritative change.

According to a further embodiment, the hybrid micro particles proposed, comprising the above-designated closed and smooth shell structure and/or the above-designated closed and hillocky shell structure, do not have any micropores as detectable via the C value determined by nitrogen adsorption. The native silicate shell of the microparticles in question is therefore lacking micropores, mesopores and macropores.

Advantages of this embodiment emerge from the fact that in contrast to open shells, the availability of the surface for molecules of different sizes is increased for the analytical or chromatographic application. It is possible, for example, for comparatively fewer larger biomolecules (larger than 1 nm) to bind to the area present in the case of open structures, then is the case for closed structures.

According to a further embodiment, microparticles are proposed which have a cavity in place of the polymer core, so that the silicon dioxide shell originally surrounding the polymer core now surrounds the cavity. The silicon dioxide shell may be either intact and closed or intact and open, in which case the microparticle is in the narrower sense a hollow sphere comprising silicon dioxide.

Advantages arise directly from the possibility of controlling the structure of the hybrid microparticles, since there is no authoritative change in the structure of the silicate shell as a result of the thermal decomposition of the core. Accordingly, then, smooth, hillocky and riven hollow spheres can be produced. In this case, however, there is no longer any definition as to whether the particles are closed or open, since the combustion of PVP may bring about an authoritative change in the pore structure.

Structurally controlled hollow silicate spheres are especially suitable for producing microscale objects which can be used as comparatively inert, robust and monodisperse mimetics or reference materials for biological or artificial vesicles or liposomes in corresponding measurement and testing methods.

According to a further embodiment, the above-described particles with a smooth or hillocky shell structure (particles P1 and P2) and with substantially pore-free surface have a specific surface area which grows increasingly with growing RF value.

Advantages of this embodiment emerge from the fact that this surface area is available for functionalization and in comparison to pure polymer particles it is possible to generate a higher density of functional groups on one particle.

According to a further embodiment, a method is proposed for producing spherical microparticles which comprise a polymer core and a shell, where the shell comprises silicon dioxide and the structure of the silicate shell has an RF value in the range from 1 to 1.5 (closed, smooth shell structure as per working example P1); an RF value in the range from 1.51 to 3 (closed, hillocky shell structure as per working example P2); or an RF value of greater than 3.01 (corresponding to the open, riven shell structure as per working example P3).

The RF value, used for the characterization or differentiation of the particles of the invention, can be determined here by first determining the external surface area of the hybrid microparticles ($A_{hybrid\ microparticle,\ external}$) minus the surface area of any micropores present, using the t method according to Lippens and de Boer. Additionally, a mean ideal surface area of the hybrid microparticle ($A_{hybrid\ microparticle,\ ideal}$) is calculated from the arithmetic mean particle diameter, which on the assumption of an ideal spherical form for all the particles can be determined by image analysis of electron micrographs of the particles. The ratio is then formed of this external surface area to the mean ideal surface area of the hybrid microparticle. The ratio obtained is referred to here as the RF value:

$$RF = \frac{A_{hybrid\ microparticle,\ external}}{A_{hybrid\ microparticle,\ ideal}}.$$

Expressed alternatively, the RF value can be calculated as a ratio of an external surface area of the hybrid microparticle that is amenable to adsorption of nitrogen to the surface area of a sphere having a diameter which is equal to the arithmetic mean diameter of the hybrid microparticles. In this case, each of the hybrid microparticles is considered to be an ideal sphere.

If there are no nitrogen adsorption data available, the RF value can be estimated from the electron micrographs. In this case, with closed shells (smooth or hillocky), an assessment is made in each case of the mean bulging of the predominantly interfused silicate nanoparticles comprising the silicate shell, and the surface area thereof is calculated. This produces theoretically possible RF values of between 1 and 2, on the assumption of silicate nanoparticles with bulging up to at most half of their diameter. The size of the silicate nanoparticles is not relevant in this case, since it is merely the bulging that determines the growth of the surface. RF values obtained for hillocky hybrid microparticles are located in some cases between 2 and 3 in real terms, as determinable by means of nitrogen adsorption. The reason for this is additional silicate nanoparticles, having bulged in some cases beyond their radius, which adhere to the silicate shell and/or have fused with this shell and/or with other nanoparticles.

The production method proposed here encompasses at least the following steps:
  preparation of polymer cores by means of a radical polymerization reaction;

coating of the polymer cores with a silicate shell, using a sol-gel process; and functionalization of an outer surface of the silicate shell with an organic chlorosilane or alkoxysilane derivative, where the preparation comprises use of a homolytically cleavable initiator selected from ACVA—or 4,4'-azobis(4-cyanopentanoic acid).

Advantages of the method encompass, as already addressed above, the superiority of the hybrid particles obtainable. A particular advantage with the use of ACVA (4,4-azobiscyanovaleric acid, CAS: 2638-94-0) as radical initiator for the polymer core synthesis arises from the fact that ACVA, as a storage-stable substance, does not require any out-of-the-ordinary precautionary measures under CLP regulation. Such measures include laboratory handling and also the protective measures on transport of the substance. Moreover, when using ACVA, carboxylic acid groups are formed on the surface of the particles. These groups ensure additional electrostatic stability of the particles, meaning that even particles with PVP of relatively low molecular weight (less than 25 000 Da) can be prepared in narrow size distributions. Furthermore, they ensure additional binding sites directly on the surface for the subsequent coating of the silicate shell, since silica intermediates and/or silicate nanoparticles are able to adhere thereto during the coating operation, by way of acid-base interactions.

According to a further embodiment, the structure of the silicate shell of the hybrid microparticle can be adjusted through an average molecular weight of the particular PVP used. Accordingly, to obtain a closed shell structure (according to P1, cf. FIG. 1a), having an RF value in the range from 1 to 1.5 and a substantially smooth outer surface, PVP with an average molecular weight of about 10 000 daltons, in other words 7000 to 11 000 daltons, is covalently bonded on the outer surface of the polymer core. To obtain a closed shell structure (according to P2, cf. FIG. 1b) with an RF value in the range from 1.51 to 3 and with a substantially hillocky outer surface, on the other hand, PVP with an average molecular weight of greater than 10 000 daltons to about 58 000 daltons, more preferably between 25 000 daltons and 58 000 daltons, is present in covalently bonded form on the outer surface of the polymer core. To obtain a substantially open shell structure (according to P3, cf. FIG. 1c), in accordance with the invention, the covalent anchoring of a PVP having an average molecular weight of more than 58 000 daltons is proposed, in which case a preferred riven structure of the silicate shell, consisting substantially of an accumulation of individual silicate nanoparticles of different but substantially uniform sizes in dense layers of varying number. In this case it is possible to establish RF values of above 3.01.

Advantages of this embodiment emerge from the fact that by the selection of the PVP stabilizer during the core particle synthesis it is possible directly to determine the structure of the silicate shell deposited on the core particles. Here, with core particles of different sizes, the shell structures formed are the same in each case; that is, there is no dependency relationship between PVP chain length and core particle size.

According to a further embodiment, in the above-stated step of "preparation of polymer cores" (cf. FIG. 6; 1), the polymer cores are synthesized in an organic solvent with a water fraction of 0 vol % up to 80 vol %, with the monomer used being a styrene, a styrene derivative and/or a comonomer having in each case at least one kind of a polymerizable double bond, with a polyvinylpyrrolidone serving to stabilize the polymer cores, and with ACVA serving as initiator.

A polymerizable double bond here is a double bond which in the presence of the initiator tends to form a radical and so enables the crosslinking of monomeric components and the formation of a polymer.

Advantages of this embodiment arise from the fact that through selection of the organic solvent and the fraction of water it is possible to influence the size of the particles. The rule here is that smaller particles are generated in the case of polar solvents (e.g., higher water fraction), and larger particles are generated in the case of less polar solvents (higher alkanes, toluene, hexane, etc.).

According to a further embodiment, the above-stated step "preparation of polymer cores" encompasses washing of the resulting polymer cores with an organic or an aqueous solvent or with a solvent mixture of organic and/or aqueous solvents (cf. FIG. 6; 1-5). The notation used here and below of successive numbers connected by hyphens denotes a sequence of the steps identified by the respective numbers in the scheme, or the synthesis pathway. Alternatively—that is, instead of the washing—there is a coating with a silicate shell and simultaneous (cf. FIG. 6; 1-2) or subsequent (cf. FIG. 6; 1-3-4) functionalization with an alkoxysilane and/or with an organic chlorosilane or alkoxysilane derivative, directly in the polymerization mixture. In other words, then, the silicate shell and or the functionalized variant thereof is grown directly in the polymerization medium, which comprises a solvent-water mixture. This synthesis pathway can be described, in accordance with the scheme in FIG. 6, by the sequence 1-2 or 1-3-4. According to methods already known, the particles are typically washed first before coating is performed. In accordance with the invention, intermediate washing steps are omitted. In that case the synthesis pathways 1-2, 1-3-4 and also, where necessary, 1-5 (simple washing) are encompassed. The shell may advantageously comprise functional groups.

Advantages of this embodiment emerge from the fact that just a few synthesis steps lead to the preparation of hybrid microparticles as described herein. The stated steps are independent of a total volume of the particular reaction mixture selected, and so microparticles can be provided in amounts that are relevant in practice, in other words on the milligram to gram scale. Likewise without problems, through the selection of relevant monomers, a controlled tailoring of the reactive groups present superficially on the polymer core is ensured.

According to another embodiment, the aforementioned step of "coating of the polymer cores" (cf. FIGS. 6; 1-5-6 and 1-5-7) encompasses the use of an alcoholic solvent-water mixture, the water fraction of the alcohol in turn being alternatively between 0 vol % and up to 80 vol %. A starting substance used for the coating is selected from an alkoxysilane (cf. FIG. 6; 1-5-7) and/or from an organic chlorosilane or alkoxysilane derivative (cf. FIG. 6; 1-5-6), with the coating taking place in the presence of a basic, an organic or an inorganic catalyst. This catalyst is selected from ammonia, sodium hydroxide and/or an organic amine, and may therefore encompass only one, two or all three of the stated compounds. Where, in accordance with the above "or" conjunction of alkoxysilane with organic chlorosilane or alkoxysilane derivative, the alkoxysilanes and organic chlorosilane or alkoxysilane derivatives are used simultaneously in the coating step, the functional groups are then incorporated in statistical distribution into the shell and are not grown on successively as consecutive layers. This opens up advantages for the control of the specificity and sensitivity of the particles for different analytes after binding of different ligands to the different functional groups.

Advantages of this embodiment arise from the fact that by means of the different water fractions, the sol-gel process is influenced and, consequently, silicate nanoparticles of different sizes are formed at different reaction rates, and then fused to form the silicate shell. It is consequently possible to enable fine adjustments to the structure of the silicate shell in accordance with the fusing of silicate nanoparticles which are of different sizes but overall have a uniform size. Additionally, by admixing of chlorosilane or alkoxysilane derivatives (cf. FIG. 6; 1-5-6), it is possible here to incorporate functional groups as well directly into the shell. Alternatively, by admixing of chlorosilane or alkoxysilane derivatives subsequent to the reaction (cf. FIG. 6; 1-5-7-8), a functional second layer is grown onto the particles. This embodiment therefore encompasses the synthesis pathways 1-5-6 and 1-5-7 as shown in the scheme, possibly with pathways subsequent thereto.

The sol-gel process comprehends an inorganic polymerization in the ethanol-water mixture, encompassing a process of hydrolysis and condensation reaction of the starting substances and of the resultant silica intermediates and silicate nanoparticles. To start with, low-chain oligomers are formed, which grow to form longer chains in the course of the reaction. From a certain point in time, which can be dictated by the reaction parameters (solvent (mixture), type and concentration of the catalyst and starting substance selected from alkoxysilane, organic chlorosilane or alkoxysilane derivatives, and mixtures thereof), the silicate nanoparticles undergo nucleation in the reaction medium and/or on the polymer core. The growth of the silicate nanoparticles on the core and/or the reaction solution has the effect, among others, of forming the silicate shells.

Advantages of this embodiment emerge from the fact that in the case of polymer cores which are prepared using PVP of relatively low molecular weight, the carboxylic acid are freely available for interaction with the silica intermediates and/or the silicate nanoparticles. As a result, the fusing of the silicate shell directly on the polymer core surface is preferred, resulting ultimately in closed, smooth shells. Furthermore, there is adsorption of resultant silicate nanoparticles with PVP polymers which are located on the surface. Consequently, in the case of medium PVP molecular weights, closed, hillocky silicate shells are formed, since the silicate nanoparticles undergo adsorption at increasing distance from the polymer core surface. In this case, reduced formation directly on the surface is assumed, since the carboxylic acids are shielded by the longer PVP chains. At high molecular weights, finally, silicate nanoparticles undergo adsorption at increasing distances from the polymer core surface, leading to the formation of open, riven structures of the silicate shells.

According to another embodiment, the aforementioned step of "coating of the polymer cores with a silicate shell" encompasses washing of the resultant hybrid microparticles with an organic solvent or an aqueous solvent or with a mixture or organic and/or aqueous solvents (cf. FIG. 6; 1-5-7-9).

According to a further embodiment, the functionalization encompasses the furnishing of the outer surface of the silicon dioxide layer with amino groups, by means of amino-group-modified organic chlorosilane or alkoxysilane derivatives (such as, for example, aminopropyltriethoxysilane, APTES) without an additional catalyst (cf. FIG. 6; 1-5-7-9-10) in a neutral reaction medium, selected from an organic solvent or an aqueous solvent or a mixture or organic and/or aqueous solvents. Since the APTES functions as catalyst, cocondensations of other silanes on the surface are also possible, if, for example, the APTES catalyzes the reaction of other silanes in solution or on the surface.

Advantages of this embodiment emerge from the fact that in this way it is easy to form multifunctional surfaces on the silicate shell. Thus, for example, two (binary), three (tertiary) or more silanes can be applied simultaneously to the surface. The mixing ratio and the total amount are then subject to further optimization. For this purpose, for example, APTES and a polyethylene glycol-modified alkoxysilane are proposed, in a mixing ratio of 1:1. Advantageously, the nonspecific adsorption of biomolecules on the hybrid particles is greatly reduced.

According to another embodiment, the functionalization encompasses furnishing with an amino group or additionally with a functional group other than an amino group, using a basic or acidic catalyst, in a reaction medium selected from an organic solvent or an aqueous solvent or with a solvent mixture of organic and/or aqueous solvents (cf. FIG. 6; 1-5-7-9-11).

Advantages of this embodiment emerge from the fact that in this way it is easy to form multifunctional surfaces on the silicate shell. Thus, for example, two (binary), three (tertiary) or more silanes can be applied simultaneously to the surface. The mixing ratio and the total amount are then subject to further optimization. For this purpose, for example, APTES and a PEG-silane are proposed, in a mixing ratio of 1:1, thereby making it possible for the nonspecific adsorption of biomolecules on the hybrid particles to be greatly reduced. Advantageously, when using APTES as catalyst, it is possible to operate in pure ethanol, in aqueous media or in solvent mixtures, without additional base or acid.

If using an additional catalyst in this reaction, the assumption is of increasingly multi-layered deposition of the functional silanes.

According to a further embodiment, the average molecular weight of the PVP used is selected from a monodisperse mixture—or, in relation to the molecular weight, a substantially homogeneous mixture—of PVP molecules of identical molecular weight. Alternatively, the reaction mixture comprises a heterogeneous mixture of PVP molecules with defined but different average molecular weights. Polyvinylpyrrolidones available commercially (including, among others, products with the trade names Kollidon® and Luviskol®) each with defined average molecular weights (average chain lengths) are advantageous. As already described, in accordance with the invention, the structure and surface area of the silicon dioxide shell, which for purposes of comparison can be defined by means of the RF value determined as described, are adjusted via the selection of the PVP in relation to its chain length and/or molecular weight.

Advantages of this embodiment emerge from the fact that, contrary to the existing practice of using PVP from a defined batch with arbitrary molecular weight, without paying any attention at all to its molecular weight, the molecular weight of the PVP in accordance with the invention is specially selected in order to bring about a defined structure of the silicate shell constructed on the polymer core.

Further advantages of the method described so far emerge from the fact that the structure (in accordance with the conditions, closed and smooth with RF values of between 1 and 1.5; closed and hillocky with RF values of between 1.51 and 3; or open and riven with RF values greater than 3.01) can be achieved independently of the diameter of the particular polymer core that is utilized.

It is advantageous, with the production method described, that in this way a broad range of hybrid microparticles is accessible that have different though always uniform sizes and different but always uniformly adjustable (resultant) density, and hence have identical sedimentation behavior, and that different but always uniformly adjustable (resultant) structure and, in association therewith, surface area are available.

According to another embodiment, the microparticles produced have a functionalized surface, the functional groups either being incorporated into the silicate shell by crosslinking (cf. FIG. 6; 1-2 or 1-5-6) or the functional groups comprising at least in sections a closed monolayer or a crosslinked multilayer of the organic chlorosilane or alkoxysilane derivative on the first silicate shell (cf. FIG. 6: 1-3-4; 1-5-7-8, 1-5-7-9-10 or 1-5-7-9-11).

Advantages of this embodiment emerge from the fact that additionally on the silicate shell it is possible to deposit a second silicon-containing layer comprising an organic chlorosilane or alkoxysilane derivative (cf. FIG. 6: 1-3-4; 1-5-7-8, 1-5-7-9-10 or 1-5-7-9-11). This second layer may optionally be so thin that it is not visible or is detectable only by means of sophisticated measurement methods (e.g. via measurements of the zeta potential).

According to another embodiment, the amino groups introduced, and/or any other functional groups introduced, are incorporated covalently and in statistical distribution into the silicate shell (cf. FIG. 7: 1-2 or 1-5-6), provided they are used concomitantly in the coating reaction as chlorosilane or alkoxysilane derivative.

Advantages of this embodiment emerge from the fact that functional groups can be incorporated into the shell just in a two-stage or three-stage process.

According to a further embodiment, the method for producing the microparticles further encompasses the burning-out of the polymer core at a temperature above 200° C. to leave the silicate shell, comprising silicon dioxide, as a hollow sphere.

Advantages of this embodiment emerge from the fact that with a suitable temperature regime, in a combustion atmosphere comprising synthetic air, with for example, for a heating rate of 5 K/min, a residence lasting at least 10 minutes, preferably lasting at least 20 minutes, more particularly lasting for 30 minutes, at 500° C., and a subsequent further increase in the temperature to up to 800° C. at a heating rate of 5 K/min, it becomes possible to burn the polymer cores completely and for the gases formed when burning the polymer cores to escape freely. The outcome of the thermal treatment proposed is the formation of hollow silicate spheres, with the structure of the surface of these hollow silicate spheres corresponding to that of the silicate shell of the native hybrid microparticles. In particular, after the thermal treatment of hybrid microparticles carried out as described, in accordance with working examples P2 and P3, the resulting hollow silicate spheres are completely intact.

According to another embodiment, the use of 4,4'-azobis (4-cyanopentanoic acid) is proposed as initiator for a radical polymerization of styrene, styrene derivatives and/or polystyrene derivatives.

Advantages of this embodiment emerge from the fact that the polymer core carries on its surface carboxylic acid groups, which to start with ensure additional electrostatic stability of the particles, allowing monodisperse particles to be obtained even with relatively low PVP molecular weights (less than 25 000 daltons). These particles mean in turn that, through the electrostatic and acid-base interactions between the carboxylic acids and the silica intermediates and/or the silicate nanoparticles, the deposition and fusion of the silicate shell takes place directly on the surface, so as to allow the formation of closed, smooth shells.

According to a further embodiment, a proposal is made to use the microparticles obtained as described as support material for chromatographic methods, more particular for permeation chromatography or affinity chromatography. The proposed chromatographic materials are characterized by a pronounced classification in terms of:
- an average diameter or a range of average diameters; and/or
- a specific surface area or a range of specific surface areas, the specific surface area being expressed in a unit which can be converted $m^2/g$; and/or
- an outer structure which is reproduced as RF value
- the nature of a functional group or mixed functional groups present on the shell, or the nature of one or more ligands bound thereto.

An average diameter here refers to an arithmetic mean of the diameter of the particles in question. Advantages of this embodiment emerge from the fact that it is possible to construct hierarchical pore dimensions, since on the one hand the size of the polymer cores can be controlled, as a first order, and also the size of the $SiO_2$ nanoparticles encompassing the silica shell can be controlled, as a second order. Additionally, through the functionalization, deliberate modification of the hierarchically constructed chromatographic material is possible.

According to a further embodiment, a proposal is made to use the hybrid microparticles produced as described, comprising a polymer core and a silicate shell surrounding the polymer core at least in sections, as support particles for a particle-based assay. The particle-based assay accordingly encompasses at least one of the hybrid microparticles described, which is characterized at least by one of the characteristics listed below:
- a mean diameter or a range of mean diameters, which can be utilized as identification of the particles on the basis of the size;
- a specific surface area or a range of specific surface areas;
- a morphological structure of the outer surface, more particularly of the outer surface of the silicate shell surrounding the polymer core, where an RF value is assignable to the structure, and the RF value is in a range from 1 to greater than 3, preferably between 1 and 3, and can be determined in accordance with the method described herein;
- a density of the hybrid microparticle that is adjustable between the ratio of the density of the polymer forming the polymer core, which is 1.05±0.1 g/ml for polystyrene, and the value of the density of the shell encompassing a silicon dioxide layer (also referred to here as silicate shell) which is 2.0±0.2 g/ml;
- a nature of a functional group or mixed functional groups present on the silicate shell, or the nature of one or more ligands bound thereto;
- an analytically analyzable signal which can be captured as a result of a specific interaction of an artificial or biological receptor, which is bound on the carrier particle, with the analyte to be detected by the assay, where an analytically analyzable signal of the assay comprises a fluorescence property.

Alternatively to the above-described classification on the basis of the structure of the hybrid microparticles, and in analogy to the working examples described, the classification may an assignment of the microparticles to an RF value lie in a range between closed with RF values of 1 and 1.5

(smooth), hillocky with RF values of between 1.51 and 3, and open with RF values greater than 3.01 (open).

Advantages of this embodiment emerge from the fact that the particles can be coded via their size, i.e., can be distinguished on the basis of the size by means of flow-cytometric or microscopic analyses. Particles of different sizes can be used alongside one another for the detection of different analytes. Likewise, according to field of application, the particular preferred structure and the associated size of the specific surface area can be adapted. For instance, open shells are more easily accessible by small molecules, and it is therefore possible here to achieve a greater density per particle, whereas, in the case of closed and smooth shells and hillocky shells, the steric shielding is reduced relative to larger biomolecules, and these in this case have better binding and or adsorption properties. Moreover, the density of the particle is adjustable, a fact which can be utilized for adaptation to the handling and colloidal properties before, during and also after the characterization and/or use. Furthermore, the light scattering of the hybrid microparticles is authoritatively determined by the polymer core. The scattering efficiency, which can be determined by means of flow cytometry, is at least as great as that of the polymer core, or is above it, depending on the silicate shell fraction.

According to a further embodiment, the use of such a support particle in a fluorescence-based measurement method is proposed, where the measurement method is selected from a method of flow cytometry or of fluorescence microscopy—in other words, for example, a method encompassing a fluorescence-optical measurement of a fluorescence intensity, of a fluorescence quantum yield, of a fluorescence decay time, of a fluorescence extinction, or of a fluorescence recovery (a measurement of the time of an increase in fluorescence, in particular up to a predetermined threshold, after an earlier extinction of fluorescence). Furthermore, the use of the hybrid microparticles is proposed in measurement methods which encompass a miniaturized variant of flow cytometry or of fluorescence microscopy in microfluidic constructions or on planar supports (chips). In this case both individual particles and particle collectives can be utilized as a platform for individual assays.

Advantages of this embodiment emerge from the fact that a fluorescence signal can be mandated, for example, via the density of loading of the microparticle (support particle) with analyte-sensitive molecules, as for example through the presence of an external surface area which is increased as a result of fissuring, this increased surface area being amenable to use for the covalent bonding of small analyte molecules or fluorophores. In another example it is possible advantageously to adjust the density of the support particles in smooth and hillocky hybrid microparticles, allowing the particles to be separated rapidly from the dispersion medium by centrifugation. This is vital for washing steps and makes it possible, in comparison to pure polymer particles in the size range of 0.5-3 µm, for example, to achieve an at least ten-fold saving in the time needed for centrifugation. The silicate shell, with correspondingly increased surface area (up to 50% in the case of smooth silicate shells and 200% in the case of hillocky silicate shells) is still available for further simple functionalization. Moreover, these silicate shells are also accessible by relatively large biomolecules.

The embodiments described can be combined arbitrarily with one another.

In accordance with the invention, the above-described embodiments make it possible, via the ratio of mass fractions of the polymer core materials forming the hybrid microparticle, and the silicon dioxide shell materials, to set, in the resultant hybrid particles, an effective density and an effective light-scattering behavior—corresponding overall in terms of forward scattering at least to that of the polymer core—which are tailored to the particular application. With the synthesis method proposed, microparticles are provided that have properties ideally adapted to the particular application.

BRIEF DESCRIPTION OF THE DRAWINGS

The appended drawings illustrate embodiments and serve together with the description to elucidate the principles of the invention.

DETAILED DESCRIPTION

Figure 1:
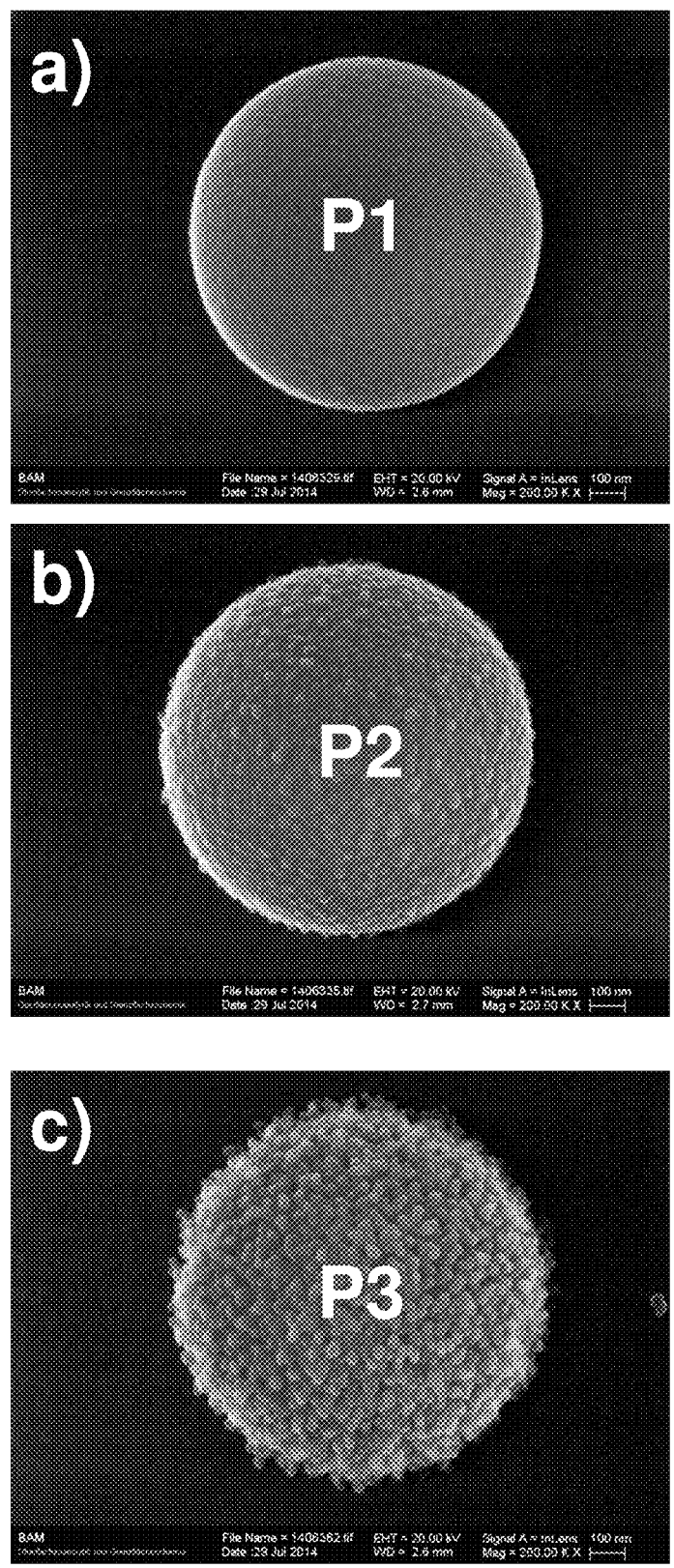
FIG. 1 shows, from top to bottom, SEM micrographs of particles with different surface structures, synthesized by the method proposed.

In particular, FIG. 1 shows in each case typical particles when imaged by means of scanning electron microscopy using an in-lens secondary-electron detector. The top picture shows particles with a smooth appearance (working example P1) whose silicate shell has an RF value of between 1 and 1.5, produced using PVP having an average molecular weight of 10 000 daltons. The middle picture shows microparticles whose silica shell has a hillocky structure (working example P2) and whose roughness factors lies substantially in the range between 1.51 and 3. Such particles were produced using PVP with an average molecular weight of 40 000 daltons. The bottom picture shows particles with open silicate shells (working example P3), in which mesopores and macropores are visible by means of the imaging techniques. These particles were prepared—as elucidated in more detail below—using PVP with an average molecular weight of 360 000 daltons. The silicate shell of the particles, formed by coagulation of different-sized silicate nanoparticles, features a structure which changes significantly from top to bottom. The three micrographs show exclusively native particles, i.e. particles not subjected to an additional heat treatment, described in detail below.

Figure 2:
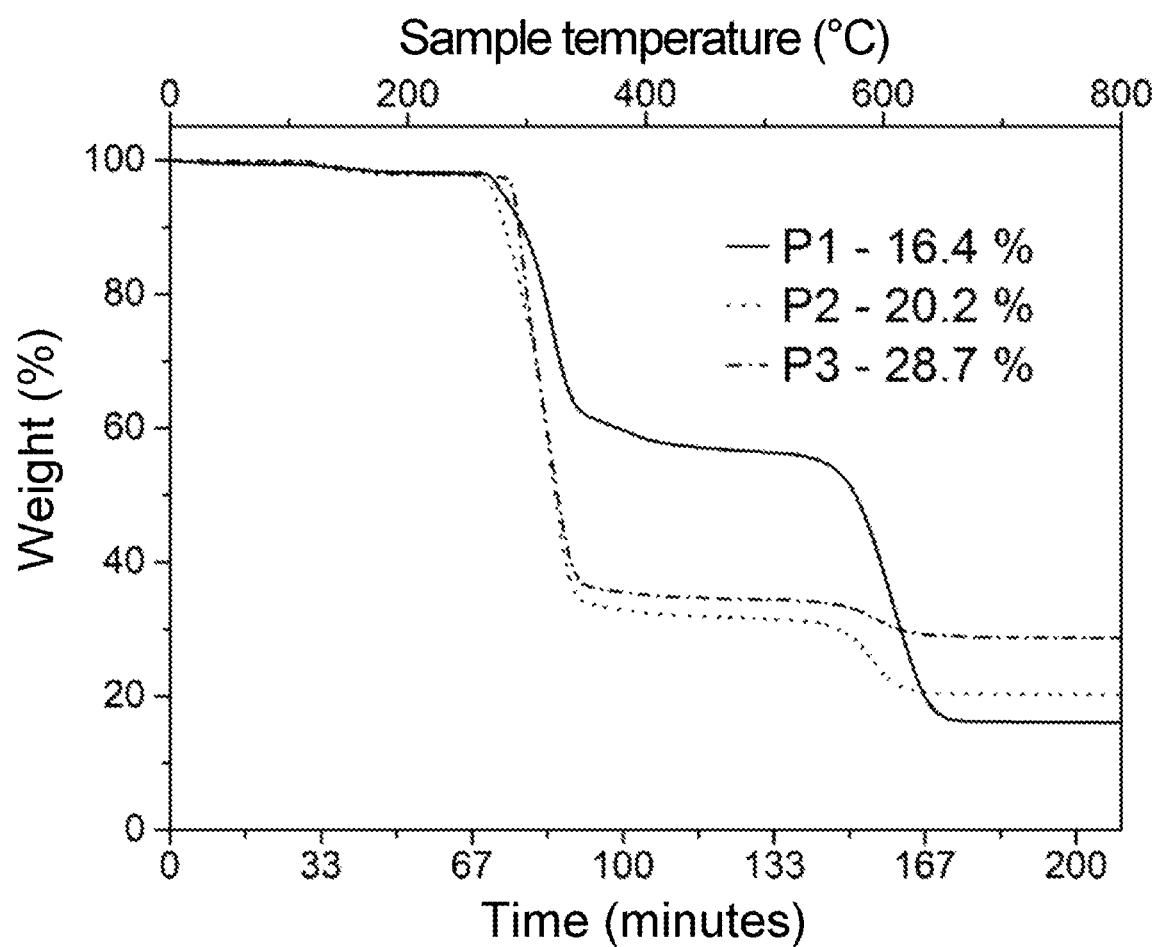
FIG. 2 shows results of the thermogravimetric analysis with synthetic air. The particles with smooth and hillocky shells exhibit increased thermal stability; the particles with a closed and smooth shell exhibit the greatest stability.

The thermogravimetric analysis in accordance with FIG. 2 comprises thermal exposure of the particles in synthetic air at a heating rate of 5 K/min. It is assumed that in the case both of P2 and of P3, PVP is intercalated between the silicate nanoparticles. If PVP is removed thermally, then corresponding pores can be formed. From the TGA plot it can be seen that the cores are protected by the shell from thermal decomposition and release, in a manner such that, in the case of P1 in particular, a part of the core undergoes measurable escape only at a temperature of 500° C. and above.

Figure 3:
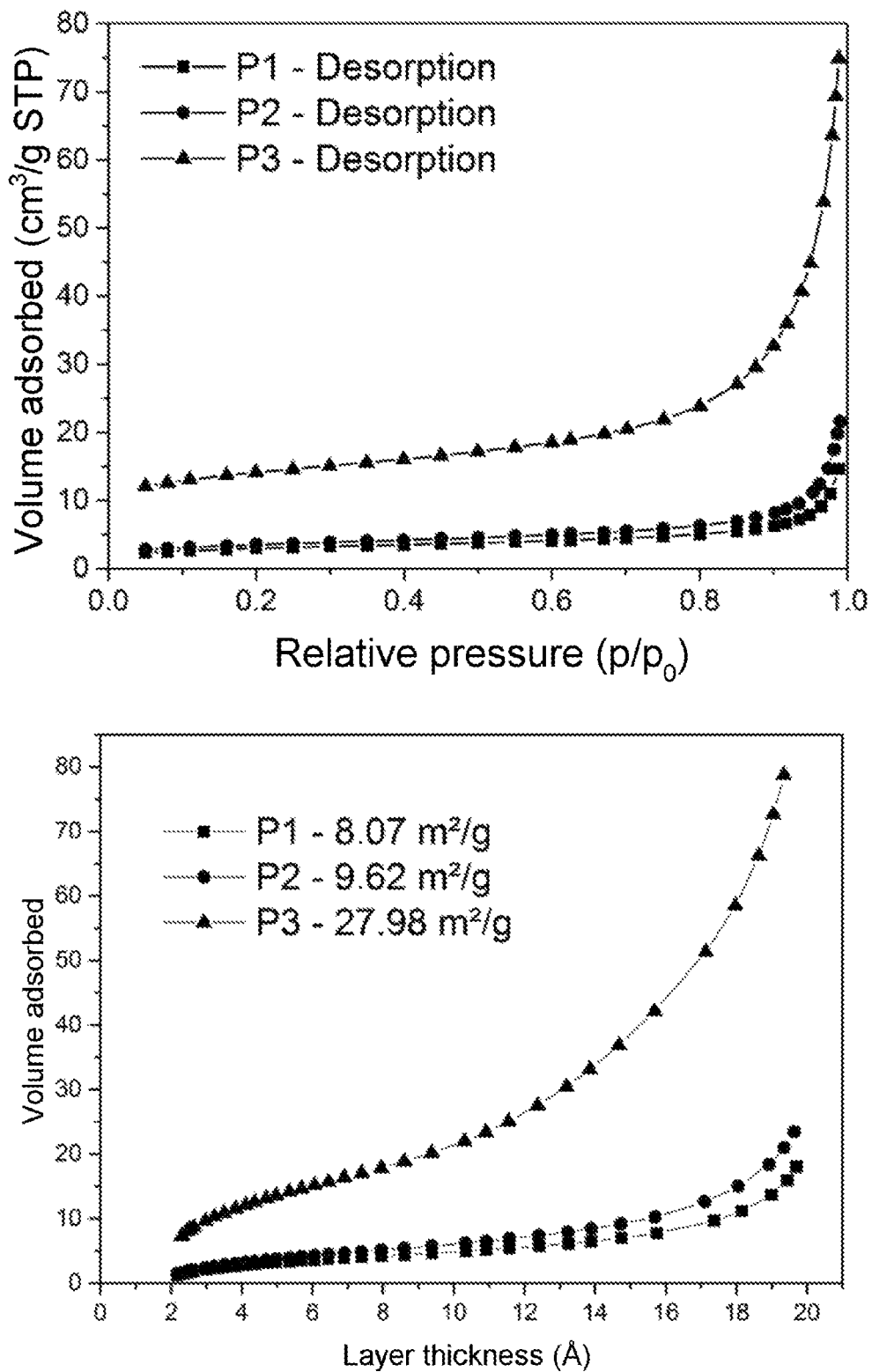
FIG. 3 shows nitrogen desorption isotherms and adsorption isotherms on particles from working examples P1, P2 and P3.

FIG. 3 shows adsorption and desorption isotherms by the method of Brunauer-Emmet-Teller (BET) of nitrogen at 77 kelvins, recorded using an ASAP 2010 (Micromeritics Instrument Corp., Norcross, Ga. (USA)). The samples, with an initial mass of at least 400 mg, were dried at 60° C. for 5 seconds in a high vacuum prior to the measurement. The external surface areas of the hybrid microparticles are calculated using the t method, for which the required conversion of (p/p0) into the adsorbed layer thickness in Angstroms took place with the aid of the Harkins and Jura approximation $$t(\text{Å}) = \sqrt{\frac{13.99}{0.034 - \log\left(\frac{p}{p_0}\right)}}$$

(cf. Harkins W D, Jura G, (1944). The adsorption data are then plotted against the layer thickness. The external surface areas per gram of the particles P1, P2 and P3 were then calculated on the basis of the slope of the linear line of best fit through the points from the resulting adsorption plot between 3.5 Å and 5 Å, and of the equation $A_{external}$=Slope× 15 468. To determine the surface area per particle, the number of particles in one gram is calculated from the mass of the polymer cores contained therein (determined from values obtained by thermogravimetry), which have an average density of 1.05 g/ml, on the assumption of an ideal sphere. The resulting external surface area per gram is then divided by the number of hybrid microparticles per gram. The figure obtained is designated in abbreviated form as $A_{hybrid\ microparticle,\ external}$.

The surface area which can be calculated starting from a mean diameter of the hybrid microparticles and on assumption of an ideal spherical form for all the hybrid microparticles (referred to hereinafter as $A_{hybrid\ microparticle,\ ideal}$) is determined as follows: a particle sample comprising more than 100 hybrid microparticles is dried at room temperature on a carbon sample-support film for transmission electron microscopy. Thereafter the sample support with the dried particle sample is imaged by means of scanning electron microscopy at 15 000× magnification and 20 kV in transmission mode. The sample does not need to be sputtered for this purpose, and so the size of the microparticles is not distorted. Micrographs obtained in a sense in transmitted-light mode for a cohort of >100 particles are represented as monochrome micrographs (bit depth: 1 bit) with the aid of suitable image analysis software, ImageJ, for example, and the area of the particles, which appear black against a white ground, is ascertained. From the area ascertained from the particles imaged, a particle diameter is computed, on the assumption that all of the particles are ideal spheres, and an arithmetic mean value of the diameter is determined from all the particles measured. This arithmetic mean particle diameter is used to calculate the ideal surface area of the hybrid microparticles in accordance with $A_{hybrid\ microparticle,\ ideal}$= $\pi \cdot d^2$.

Ultimately here, as elucidated above, an RF value of 1.33 was obtained for particles from working example P1, an RF value of 1.72 for particles as per working example P2, and an RF value of 4.84 for particles as per working example P3.

Figure 4:
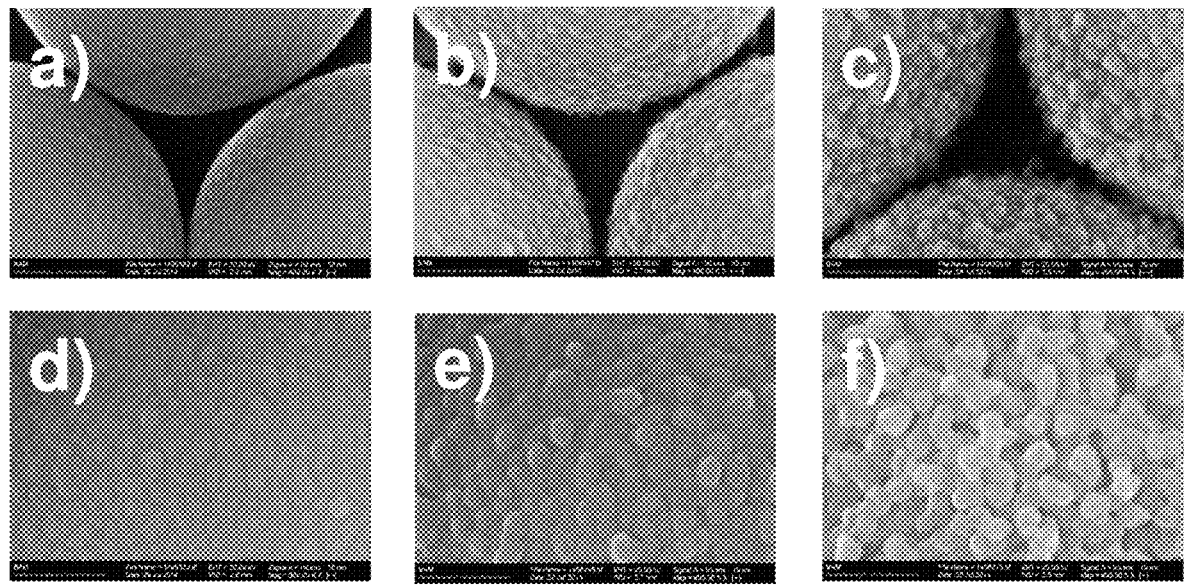
FIG. 4 shows micrographs of the surface of the silicate shell of typical particles, by means of scanning electron microscopy (SE detector)

FIG. 4 shows scanning electron micrographs of the surface of the silicate shell of typical particles (SE detector).

Figure 5:
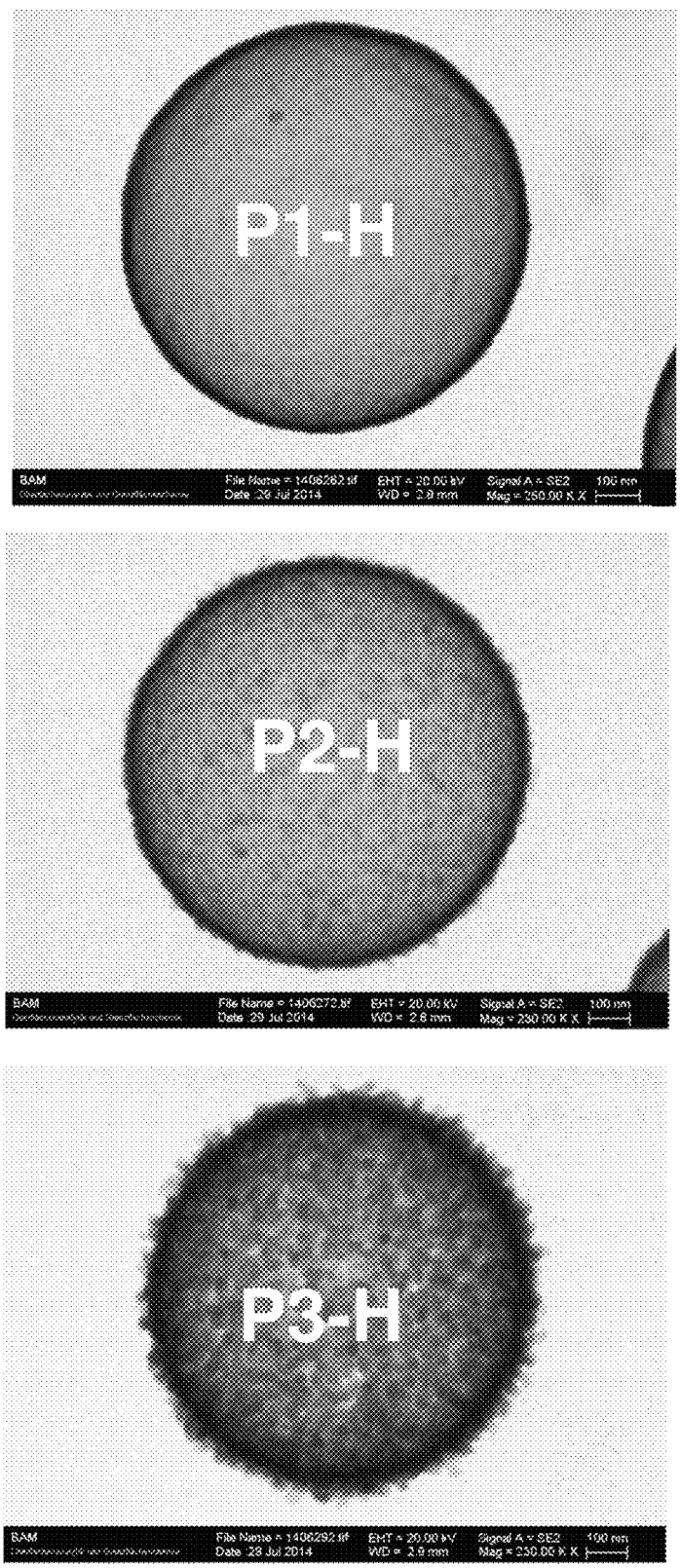
FIG. 5 shows, from top to bottom, SEM micrographs of thermally treated microparticles; particles with smooth appearance as per working example P1-H, whose RF values in the native state, i.e. before thermal treatment, were around 1.3. The middle picture shows particles from working example P2-H. The native particles (P2) are prepared using PVP with an average molecular weight of 40 000 daltons, and before the thermal treatment had a hillocky surface with an average RF value of 1.7. The bottom picture depicts particles as per working example P3-H, which in the native state, before the thermal treatment, a silicate shell, described here as open and riven, and an RF value of about 4.8. The particles P3 were produced with PVP having an average molecular weight of 360 000 daltons, and then subjected to thermal treatment. The thermal treatment, identical for all three particle classes, encompassed a gradual combustion of the polymer core in synthetic air at a heating rate of 5 K/min up to 800° C. with a subsequent constant combustion time of 1 hour at 800° C.
Figure 6:
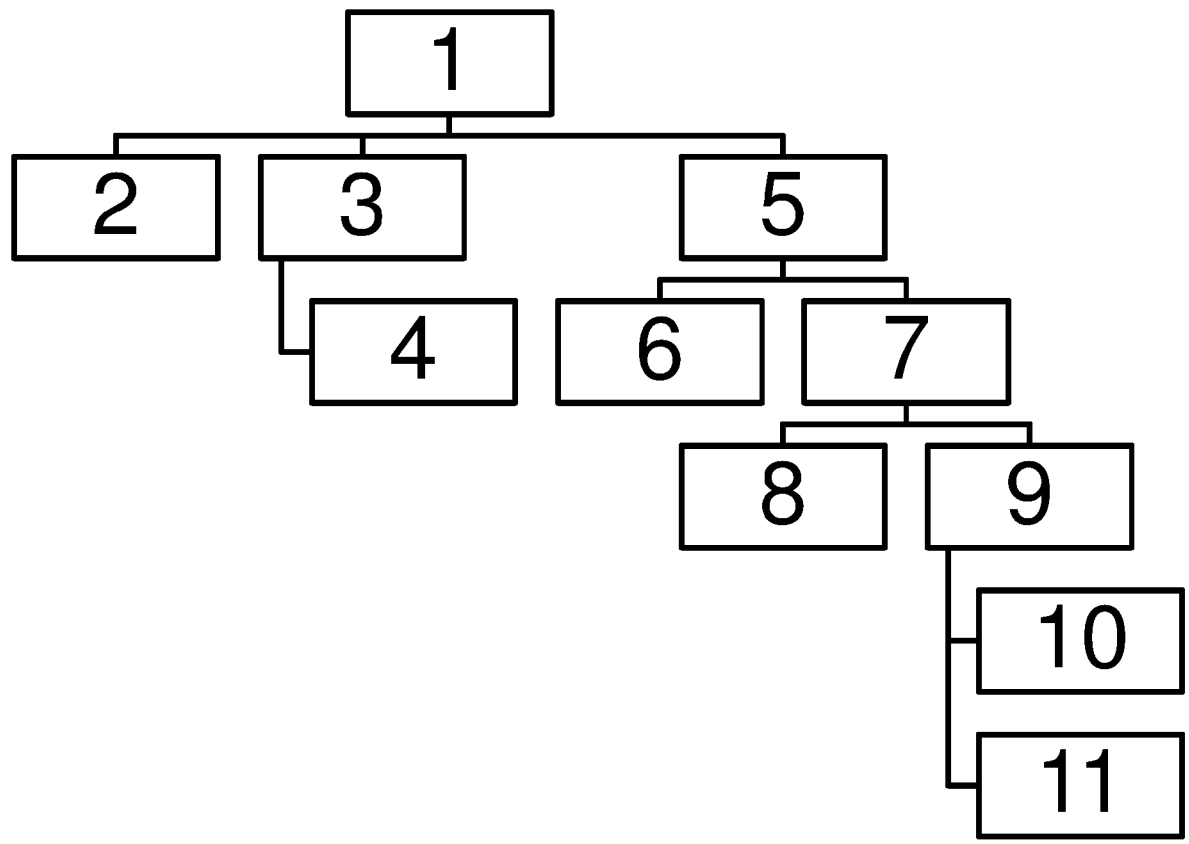
FIG. 6 shows a scheme of the synthesis pathways proposed in accordance with the invention for the core-shell particles described here.

FIG. 5 shows, from top to bottom, scanning electron micrographs of thermally treated microparticles. The topmost image shows particles with a smooth appearance as per working example P1-H, whose RF values in the native state, i.e. before thermal treatment, were in the region of around 1.3. The middle picture shows particles from working example P2-H, in the form in which they are present after a thermal treatment of native particles produced in accordance with working example P2 using PVP with an average molecular weight of 40 000 daltons. Before the thermal treatment, they had a hillocky surface with an average RF value of 1.7. The bottom picture depicts particles as per working example P3-H, which in the native state before the thermal treatment have a silicate shell, referred to here as open and riven, and an RF value of about 4.84. The particles P3 were prepared using PVP K360 (PVP with an average molecular weight of 360 000 daltons) and were then thermally treated. The thermal treatment, identical for all three particle classes, encompassed a gradual combustion of the polymer core in synthetic air at a heating rate of 5 K/min up to 800° C. with a subsequent combustion taking place constantly at 800° C. over a time of 1 hour.

Figure 7:
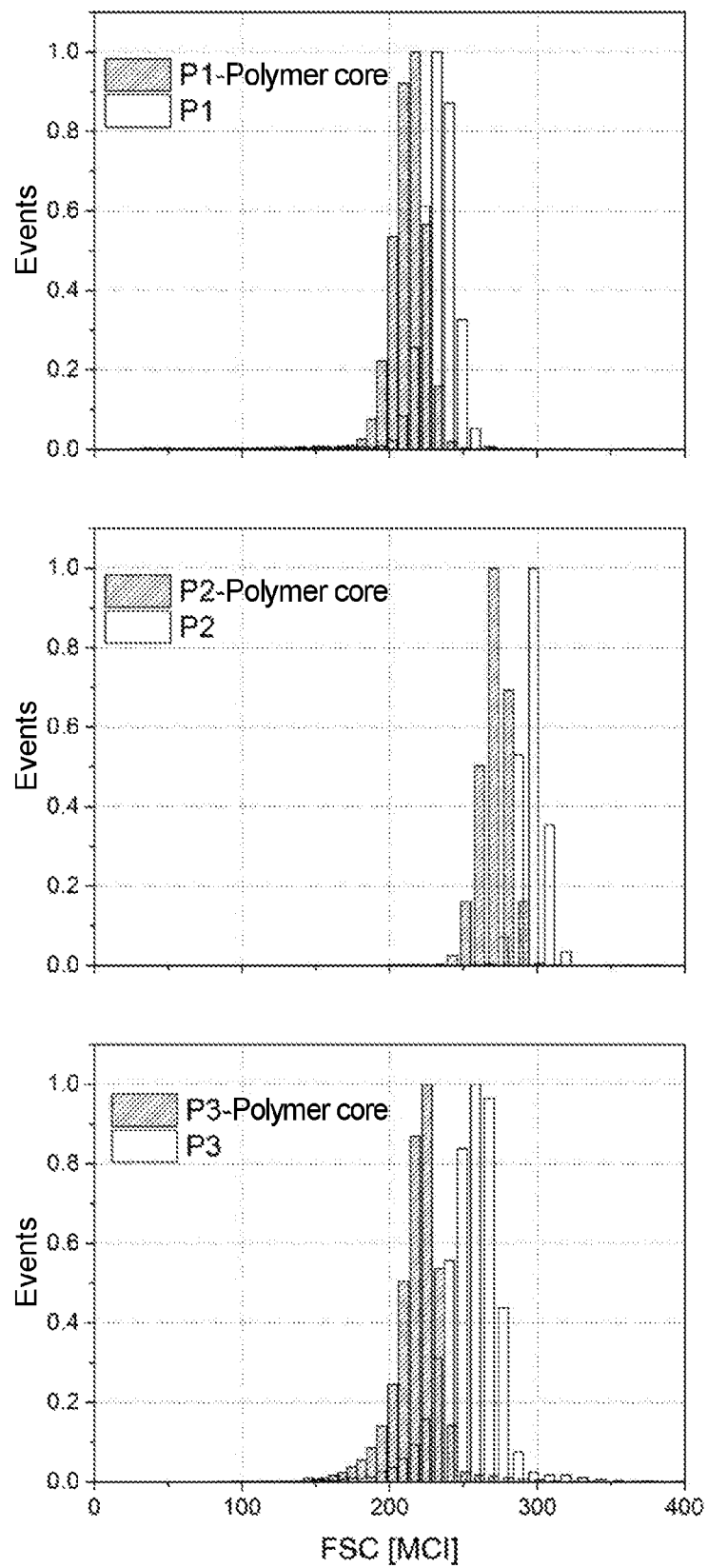
FIG. 7 shows scattered light signals (FSC) of the hybrid particles in comparison to the scattered light signals (FSC) of the corresponding polymer cores, in each case in a flow cytometer. The abbreviation MCI here stands for the mean channel intensity.

FIG. 7 shows scattered light signals of forward-scattered light (FSC) of the microparticles (comprising polymer core and silicate shell) in comparison to the respective polymer cores, in a flow cytometer. Comparing the samples, it becomes apparent that the scattered light intensity increases at constant distribution, and is therefore at least above that of the pure polymer core.

Hybrid particles are known from publications U.S. Pat. No. 6,103,379 and Bamnolker, Nitzan et al. 1997. Described exclusively, however, is the use of long-chain PVP (360 000 daltons), leading to the formation of hybrid microparticles having an open, riven structure to the silicate shell. From the TGA data, the average size of the silicate nanoparticles and of the polymer core, which is employed here as a reference value for determining the average surface area of the hybrid microparticles, it is possible to calculate RF values of 3.66, 5.92 and 8.15. The authors Hong, Han et al. (2008) describe the use of PVP with an average molecular weight of 40 000 daltons for the direct coating of polymer cores using the toxic and environmentally damaging AIBN. Core-shell particles produced with short-chain PVP (Mw less than 40 000 daltons) are unknown. None of the aforesaid publications provides any indication of an influence on the structure of the silicate shell through the PVP, which is used exclusively to stabilize the core particles. And there are certainly no indications of any influence by the molecular weight of the PVP used on the fine structure of the shell. Instead, PVP is used merely as a stabilizer. An effect of the stabilizer on the processes which occur during silicate coating was unknown.

With regard to the utilization of the hybrid microparticles obtained, applications contemplated are those hitherto-typical applications for surface coatings or the generation of colloidal crystals. The hybrid microparticles have been used much more rarely in analytical applications based on individual particles. Examples in this case are lanthanoid-doped polymer beads, provided with a silicate shell for better functionalization (Abdelrahman 2011). The polymer cores are prepared here with a hydrophobic initiator, PVP (MW ~54 000 daltons) and additional costabilizer, and feature silicate shells with a thickness of above around 150 nm. Other examples are quantum dot-functionalized beads (Cao, Huang et al. 2006) or Raman-coded beads (Jun, Kim et al. 2007), which are coated with a silicate shell and then used in analytical assays. Here, no PVP is used in the synthesis of the polymer core, and the coating takes place after the sulfonation of the polymer cores, with no control over the structure, density or light-scattering qualities of the hybrid microparticles.

The aforesaid approaches do not offer any synthesis route with general validity for the controlled preparation of native hybrid microparticles having an adjustable size within the relevant range between 0.5 and 10 μm and a narrow size distribution, structure, density and light-scattering properties for the application of the hybrid microparticles in flow-cytometric methods or related miniaturized variants. The initiator normally used for the radical polymerization of the polymer cores is AIBN ((2,2'-azobisisobutyronitrile), which is environmentally burdensome and toxic. Moreover, it is not possible here to produce monodisperse particles with PVP (less than 25 000 daltons), which is needed for the preparation of closed and smooth surfaces and hence for the acquisition of the entire structural range with RF values of between 1 and greater than 3, as for example between 1 and 10.

Proposed in accordance with the invention, via the provision of hybrid microparticles comprising a polymer core and a silicon dioxide shell (here also called silicate shell) at least partly surrounding the polymer core, is the combining of the advantages of the organic polymer of the core and of the silicon dioxide of the shell in an assembly of materials, in order:

a) to utilize the advantages of the polymer core synthesis in a radical polymerization by means of ACVA for preparing particles with different sizes of between 0.5 and 10 μm with a sufficiently narrow size distribution;

b) to control the effective density of the hybrid microparticles, which is authoritatively determined by the mass fraction of the polymer core and of the silicate shell and is between 1.05 and 1.8, but preferably between 1.09 and 1.53;

c) to maintain at least the scattered-light intensity of the particles in comparison to polystyrene, but also, moreover, to increase the intensity by the grown addition of a silicate shell in accordance with the mass fraction;

d) to be able to bring about a fluid adjustment to the structure of the silicate shell, in a range between closed and smooth to hillocky, corresponding to RF values of the microparticles of between 1 and 3, through to open and riven, with RF values of greater than 3.01, on the basis of the selection of the average molecular weight of PVP;

e) to authoritatively determine the external surface area accessible by a potential analyte, and the functional groups of the hybrid microparticles that are anchored to that external surface via a linker or are directly present thereon, through the structure and associated surface area of the silicate shell. The word "authoritatively" in this context also describes the option whereby, in addition to a silicon dioxide shell at least partly covering the core, with the surface area thereof accessible from the outside, there are also fractions of the surface of the polymer core that are freely accessible. The freely accessible fractions of the surface of the polymer core can be modified chemically in accordance with the methods known for the respective polymer, and, as and when required, may be furnished with at least one kind or two or more kinds of ligands or with a mixture thereof. Ligands are understood to include biological receptors (antibodies, antibody fragments or peptides, reactive proteins, DNA or DNA-based biopolymers, (poly)sugars, or mixed conjugates thereof), analyte-selective groups, analyte-sensitive groups or groups with analyte affinity, fluorescent dyes, molecular probes, atom clusters, quantum dots, organic or further inorganic nanoparticles such as, for example metal nanoparticles or metal-oxidic nanoparticles.

(f) to raise the chemical and physical stability of the particles, as a result of the at least partial envelopment with the silicon dioxide shell, relative to that of the pure polymer core.

(g) to furnish the accessible external silicatic surface and the functional groups anchored thereto via a linker, or present directly bound thereon, as and when required, with at least one kind or two or more kinds of ligands or with a mixture thereof. Ligands are understood to include biological receptors (antibodies, antibody fragments or peptides, reactive proteins, DNA or DNA-based biopolymers, (poly) sugars, or mixed conjugates thereof), analyte-selective groups, analyte-sensitive groups or groups with analyte affinity, fluorescent dyes, molecular probes, atom clusters, quantum dots, organic or further inorganic nanoparticles such as, for example, quantum dots, metal nanoparticles or metal-oxidic nanoparticles. Furthermore, the grown addition of a further polymer layer on the silicate shell is proposed, such as the growing-on of a molecularly imprinted polymer layer (MIP), for example.

The method proposed provides spherical hybrid microparticles whose surface, on the basis of its physical nature as a silicate surface, is readily amenable to a respectively desired chemical modification with organic chlorosilane or alkoxysilane derivatives, exhibiting a sufficiently high difference in refractive index relative to water, an optimized propensity toward sedimentation in aqueous solutions, and a narrow size distribution.

Advantageously, the proposed concept of the hybrid microparticles makes possible a more readily manageable synthesis, in accordance with the proposed method comprising the use of the initiator ACVA, since the initiator is less environmentally burdensome and toxic by comparison with AIBN. Moreover, in the case of transport, additional costs for the transmission of hazardous goods, which are incurred in the case of AIBN, are not incurred. The synthesis presented here allows precise control over the fine structure of the silicate shell. In particular, it is possible to establish a surface of the outer particle surface area from closed and smooth (RF values of between 1 and 1.5) through closed and hillocky (RF values of between 1.51 and 3) up to open with RF values of greater than 3.01. Likewise, with the production method proposed here, it is also possible to produce open structures with lower RF values of less than 3, provided an incomplete monolayer of silicate nanoparticles is applied to polymer cores which have been produced using PVP with an average molecular weight of 10 000 Da or PVP with an average molecular weight of 40 000 Da. Otherwise, the RF values may also be greater than 3, but not more than 4, if a complete monolayer is present. This is possible with a relatively small amount of TEOS (ratio of TEOS to amount of PS used: less than 3:1). These structures, however, are not very suitable for analytical application, since silicate nanoparticles which have not fused to form closed shells have a tendency to part from the core. Lastly, such monolayers can also not be referred to as smooth, and would, in analogy to P3, suffer from reduced accessibility by large molecules.

In accordance with practical working examples, the core particles are prepared in a dispersion polymerization in EtOH (96%). For this purpose, first 1.7 g of the PVP (equal amounts in the case of PVP with different molecular weights) are dissolved in 100 ml of EtOH in a 250 ml three-neck flask, equipped with an oval magnetic stirrer, at 75° with stirring at 250 rpm. At the same time, in a 50 ml glass beaker, 5 ml of styrene (alternatively other amounts of styrene, between 5 and 50 ml, corresponding to a volume fraction of 4-42% in comparison to the amount of EtOH used, for the preparation of larger particles) and 95.4 mg of ACVA (2.1% by weight to the amount of styrene used) are dissolved in 20 ml of EtOH. The two solutions are then flushed simultaneously with argon for 30 minutes. Subsequently the ACVA-styrene solution is added to the preheated PVP solution. The polymerization is carried out over 24 hours at 75° C. with a stirring speed of 250 rpm. The reaction mixture is then left to cool for 30 minutes, after which the particles obtained are separated from the reaction medium by centrifuging. Here, the reaction mixture is divided between 50 ml centrifuge vessels and centrifuged at 4000 RCF (relative centrifugation force) for 10 minutes. The supernatant is removed and the particles are redispersed in 30 ml of methanol in each centrifuge vessel. The methanol is subsequently replaced 2× in each case in order to separate the particles from impurities. The polymer cores are subsequently dried in a vacuum oven for 12 hours.

For the preparation of closed and smooth hybrid particles, PVP with an average molecular weight of 10 000 daltons is used in the polymer core synthesis. For the preparation of closed and hillocky hybrid particles, PVP with an average molecular weight of 40 000 daltons is used in the polymer core synthesis. For the preparation of open and riven hybrid particles, PVP with an average molecular weight of 360 000 daltons is used in the polymer core synthesis.

In accordance with practical working examples, the core particles are coated with a silicate shell in a sol-gel process under Stöber-like conditions (ethanol-water mixture and ammonia as catalyst). For this purpose, 50 mg of polymer cores are dispersed in 5 ml of EtOH and 0.1 ml of water in a glass beaker with a capacity of 15-20 ml. Then 150 µl (in a ratio of 3:1 to the amount of polymer core used) of TEOS and 150 µl of ammonia (concentrated, 32%) are added. The coating reaction is carried out with stirring using a magnetic stirrer at 500 rpm. After 18 hours, the hybrid core particles obtained are transferred to a 5 ml vessel with a snap-fastening lid (Eppendorf) and separated from the reaction medium by centrifuging at 4000 RCF for 5 minutes. The particles are washed twice with 3 ml of water and once with 3 ml of EtOH (96%) by centrifuging (4000 RCF, 5 minutes) and redispersing in the wash medium. Following centrifugation and separation from EtOH, finally, the particles are dried in a vacuum oven at room temperature for 4 hours.

In accordance with the practical working examples P1, P2 and P3, described above in paragraph [0042], different particles P1, P2 or P3 are obtained, according to which polymer cores were used in the coating reaction.

TABLE 1

| Working example | P1 | P2 | P3 |
|---|---|---|---|
| Calculated surface area (hybrid microparticle) | 2.74 µm² | 3.25 µm² | 3.18 µm² |
| Measured surface area hybrid particle (t-plot) | 3.65 µm² | 5.60 µm² | 15.40 µm² |
| RF value | ~1.33 | ~1.72 | ~4.84 |
| RF value range (class) | 1-1.5 | 1.51-3 | greater than 3.01 |

A categorization of the microparticles in greater detail may be undertaken in accordance with the micropores, mesopores and macropores that are observed and are verified by means of nitrogen adsorption, for example (cf. Tab. 2):

TABLE 2

| Topography | Working example | Presence of micropores | RF value | Presence of meso- and/or macropores |
|---|---|---|---|---|
| smooth | P1 | No<br>C value ≈ 160 | 1.33 | No |
| hillocky | P2 | No<br>C value ≈ 158 | 1.72 | No |
| open | P3 | Yes<br>C value ≈ 369 | 4.84 | Yes |

The C value is determined by means of nitrogen adsorption and provides information on the presence of micropores, since only at values between C=50 and C=150 is it possible to assume a nitrogen adsorption which can be described reliably by a B.E.T. adsorption isotherm, and the absence of micropores (Rouquerol et al., 1999).

The values determined for working examples P1 and P2 are just above this. Minimally, therefore, there could be pores present, since the C value here is in each case a little over 150 (see Table 2). Up to a value of 200, therefore, closed particles without micropores are defined. P3 exhibits increased microporosity and also, independently thereof, meso-/macropores which are detectable by means of imaging methods (cf. FIG. 4-f), the particle being consequently categorized as open.

Micropores are also accessible by nitrogen. The critical factor here is that the surface area is characterized by means of nitrogen adsorption, but in that case by the t method for determining the fraction of the external surface area, or by assessing the surface area by means of imaging analyses. A distinction is to be made here between closed shells, where only the bulging of the silicate nanoparticles is assessed, or open shells, where the external surface area is provided by the summing of the surface areas of the individual silicate nanoparticles. As elucidated below, comparable results are achieved here. An objective assessment and categorization is also possible in this way for the particles stated in other patents and publications.

On the basis of the desorption isotherms (cf. FIG. 3), however, no mesopores as such are measurable, since otherwise a type IV isotherm would have been expected. Nevertheless, pore sizes of below 50 nm are visible by means of imaging methods (cf. FIG. 4-f). An open assembly of silicate nanoparticles can therefore be assumed, surrounding the silicate shell.

As shown in FIG. 3, the hybrid particles have an increased measurable specific surface area. The surface areas here were determined on the basis of the T method, which differentiates external surfaces from surfaces resulting from micropores. For this purpose, using the Harkins-Jura approximation, the relative pressures are converted into layer thickness of the adsorbed nitrogen molecules. The data obtained by means of nitrogen adsorption are then plotted against the calculated layer thicknesses. On the basis of the slope, obtained by linear regression of the data points between 3.5 Å and 5 Å, corresponding to the range between the formation of a monolayer and the onset of capillary condensation, the external surface area is calculated. For determining the surface area per particle, the number of particles in 1 gram is calculated from the mass of polymer core contained therein (determined via the TGA values) on assumption of an ideal sphere. The external surface area per gram that is obtained is then divided by the number of hybrid microparticles per gram, to give the external surface area per particle.

The hybrid microparticles according to P1, identified here as closed and smooth, have a surface area increased by 33% relative to the pure polymer cores (according to an RF value of 1.33); the closed hillocky hybrid microparticles according to P2 have a surface area increased by about 72% (according to an RF value of 1.72). In the case of ideal occupancy of the polymer cores with silicate nanoparticles which have fused to form a closed, hillocky silicate shell, and which have undergone bulging up to half of their diameter, a maximum RF value of 2 is anticipated. RF values for a closed, hillocky structure of the silicate shell that are above 2 and below 3 are obtained if silicate nanoparticles with more than half the diameter protrude in isolation from the closed shell.

Open, riven structures according to P3 have a surface area increased by 384% relative to pure polymer cores (according to the RF value of 4.84). The surface area determined by means of nitrogen adsorption using the t method corresponds approximately here to the sum of the surface areas of the core and an accretion of around 3520 silicate nanoparticles with a size of around 35 nm. The number of silicate nanoparticles was calculated on the basis of the silicate fraction, measured by TGA, for a particle at a level of 28.7% with the average diameter of 893.5 nm. Determination of the RF value on the basis of the T method or by means of imaging methods therefore leads to comparable results, thus enabling an objective categorization of hybrid core-shell particles using nitrogen adsorption data or image analyses.

The surface area adjustably increased in each case can be exploited for analytical use, by the possibility, for example, of covalent anchoring of small and of larger molecules, utilizable as scavengers and/or receptors, or of a further polymer layer with a high density/microparticle and/or with a defined density per unit area.

Furthermore, however, the specifically established particle density can also be utilized in order to provide particles having properties adapted in each case to a specific analytical task. For instance, particles with a density of greater than 1.05 undergo more rapid sedimentation in water, and/or have a significantly more rapid sedimentation behavior on centrifuging, and this may mean considerable time savings especially for washing steps during production, functionalization and use.

Lastly, a feature of the hybrid particles is that their light-scattering properties are authoritatively influenced by the polystyrene core, the light-scattering intensity therefore corresponding at least to that of the polystyrene core. This can be confirmed (FIG. 7) on the basis of the scattered-light intensity distribution as measured by means of flow cytometry. Measured in this case at each instance is an increase in scattered-light intensity, with retention of the scattering properties and of the scattered-light distribution. It can be assumed that the mass fraction of silicate in the hybrid microparticle correlates with the increase in the scattered-light intensity.

In accordance with the invention, the polymer core is prepared in the presence of polyvinylpyrrolidone (PVP) by radical polymerization in alcoholic solvent with a possible water fraction of 0-80%, starting from styrene and/or from a mixture of styrene and other polymerizable comonomers. The radical polymerization initiator used at 75° C. is a homolytically cleavable initiator, preferably ACVA (ACVA=4,4'-azobis(4-cyanovaleric acid), or 4,4'-azobis(4-cyanopentanoic acid)). Advantageously, ACVA is less toxic to humans and the environment and, moreover, it equips the polymer core with carboxylic acid groups, which ensure additional stabilization during the polymerization, and for this reason polymer cores with PVP of relatively low molecular weight, of less than 25 000 Da, can also be produced in narrow size distributions. The coating of silicon dioxide takes place after washing of the core particles with organic or aqueous solvent in a sol-gel process in alcohol/water mixtures with alkoxysilanes in pure form, or in a mixture of these as starting substances and alkaline initiators such as ammonia, sodium hydroxide or organic amines.

Surprisingly it has emerged that the molecular weight of the polyvinylpyrrolidone used as a stabilizer during the polymerization authoritatively influences the structure of the silicate shell. In particular, depending on the average molecular weight of the PVP, it is possible to configure the surface of the silicate shell, alternatively, from a closed and smooth or hillocky surface to an open surface, in which case short chains (average molecular weight 10 000 daltons) lead to a closed and smooth shell structure, medium chain lengths (average molecular weight 40 000 daltons) lead to a closed and hillocky shell structure, and long chains (average molecular weight 360 000 daltons) lead to an open and riven shell structure (cf. FIGS. 1-*a* to 1-*c*, and FIGS. 4-*a, d* or FIGS. 4-*b,e* and FIGS. 4-*c,f*).

From a scientific and technical standpoint, the proposed hybrid microparticles with adjustable size in conjunction with narrow size distributions, precisely controllable densities, suitable light-scattering properties, and also structure and surface of the silicate shells represent an innovative and improved spherical platform particularly for particle-based analytical applications.

By means of the size of the polymer cores it is possible to code the particles for a multiplex application. An illumination property can also be used for coding, by using fluorescent comonomers.

Fluorescent molecules or fluorescent organic and/or inorganic nanoparticles may also be integrated into the core, for dye coding, statistically and not covalently, by way of swelling techniques, for example. This brings about possibilities of post-coding after core particle synthesis.

The deliberate adaptation of the densities makes it possible to control the sedimentation behavior of the particles, according to the analytical application, for increased colloidal stability at relatively low densities (e.g. between 1.05 and 1.25) or for more rapid separation of the particles by means of centrifugation, in the case of increased densities (e.g. between 1.1 and 1.5).

The scattered-light intensity in flow-cytometric applications of the hybrid microparticles is equivalent at least to that of pure polystyrene, or even above, depending on the mass fraction of the accreted shell. In comparison to pure silicate microparticles, therefore, the hybrid microparticles yield higher light-scattering intensities for a given size.

At the same time, the hybrid microparticles provide a silicatic surface which can be functionalized by modification in situ or afterward. As a result, it is possible to generate not only individual functional groups but also deliberate mixed surfaces on the hybrid microparticle surface, and these can be optimized advantageously in each case for the analytical issue at hand.

The structure of the silicate shell can be adjusted, finally, in a controlled way via the selection of the polymer cores, stabilized by PVP with different molecular weights. Closed, smooth and closed, hillocky structures here are more accessible by larger molecules in the case of surface area increase of up to 200%. Conversely, open and riven silicate shells are less accessible for large molecules, but do display the greatest increases in surface area, thereby making the adaptation of small molecules advantageous here.

The present invention has been elucidated with reference to working examples. These working examples should in no way be understood as imposing any limitation on the present invention. The claims which follow represent a first, non-binding attempt to define the invention generically.

REFERENCES

Abdelrahman, A. I. (2011). Lanthanide-encoded polystyrene microspheres for mass cytometry-based bioassays. Doctor of philosophy, University of Toronto.
Bamnolker, H., B. Nitzan, et al. (1997). "New solid and hollow, magnetic and non-magnetic, organic-inorganic monodispersed hybrid microspheres: synthesis and characterization." Journal of Materials Science Letters 16(16): 1412-1415.
Cao, Y. C., Z. L. Huang, et al. (2006). "Preparation of silica encapsulated quantum dot encoded beads for multiplex assay and its properties." Analytical Biochemistry 351(2): 193-200.
Harkins, W. D., and Jura, G., J. Chem. Phys., 11, 430 (1943); J. Amer. Chem. Soc., 66, 1362 (1944).
Hong, J., H. Han, et al. (2008). "A Direct Preparation of Silica Shell on Polystyrene Microspheres Prepared by Dispersion Polymerization with Polyvinylpyrrolidone." Journal of Polymer Science Part A: Polymer Chemistry 46(8): 2884-2890.
Jun, B.-H., J.-H. Kim, et al. (2007). "Surface-Enhanced Raman Spectroscopic-Encoded Beads for Multiplex Immunoassay." Journal of Combinatorial Chemistry 9(2): 237-244.
Lippens, B. C.; de Boer J. H. (1965) Studies on pore systems in catalysts: V. The t method. Journal of Catalysis 4(3) 319-323
Rouquerol, F.; Rouquerol, J.; Sing, K.: Adsorption by Powders and Porous Solids, Elsevier, 1999 (ISBN: 978-0-12-598920-6).
S. Lowell, Joan E. Shields, Martin A. Thomas, Matthias Thommes: Characterization of Porous Solids and Powders: Surface Area, Pore Size and Density, Particle Technology Series, Kluwer Academic Publishers (2004), p. 130-132; ISBN 1-4020-2302-2
U.S. Pat. No. 6,479,146 B1 (Fabrication of multilayer-coated particles and hollow shells via electrostatic self-assembly of nanocomposite multilayers on decomposable colloidal templates);
U.S. Pat. No. 6,103,379 A (Process for the preparation of microspheres and microspheres made thereby)

The invention claimed is:

1. A hybrid microparticle comprising a polymer core and a shell which surrounds the polymer core and which comprises a silicon dioxide layer;
characterized by an RF value, the RF value being defined as the ratio of an external surface area amenable to the adsorption of nitrogen to a surface area which is computable from an arithmetic mean diameter of the hybrid microparticle considered as an ideal sphere according to the formula $$RF = \frac{A_{hybrid\ microparticle\ external}}{A_{hybrid\ microparticle\ ideal}};$$

wherein a polyvinylpyrrolidone having an average molecular weight is covalently linked to the polymer core;
wherein the shell comprising the silicon dioxide layer is disposed directly on the polymer core; and
wherein the shell has a structure selected from:
closed and smooth, with the shell having an RF value of between 1 and 1.5 if the average molecular weight of the polyvinylpyrrolidone is 10 000 daltons; and
closed and hillocky, with the shell having an RF value of between 1.51 and 3 if the average molecular weight of the polyvinylpyrrolidone is 40 000 daltons.

2. The hybrid microparticle according to claim 1, wherein the structure of the shell is closed and in a native state has no pores,
has no micropores, characterized by a pore diameter of less than 2 nm;
has no mesopores, characterized by a pore diameter of between 2 nm and 50 nm; and
has no macropores, characterized by pore diameters of greater than 50 nm.

3. The hybrid microparticle according to claim 1, wherein the polymer core of the microparticle comprises a polymer component selected from polystyrene, a polystyrene derivative and/or a comonomer, where at least one polymer component has a polymerizable double bond, so that the polymer core of the microparticle can be formed by polymerization of at least one polymer component.

4. The hybrid microparticle according to claim 1,
wherein the RF is in the range from 1 to 1.5 and the polyvinylpyrrolidone has an average molecular weight in the range from 7000 daltons to 11 000 daltons or
wherein the RF is in the range from 1.51 to 3 and the polyvinylpyrrolidone has an average molecular weight from 25 000 daltons to 58 000 daltons.

5. The hybrid microparticle according to claim 1, the polyvinylpyrrolidone forming a layer between the polymer core and the silicon dioxide shell.

6. The hybrid microparticle according to claim 1, wherein the shell comprising the silicon dioxide layer is joined via hydrogen bonds to the PVP.

7. The hybrid microparticle according to claim 1, wherein the shell has an increased specific surface area by comparison with the polymer core,
wherein an RF value of 1.33 for hybrid microparticles with a closed and smooth shell structure corresponds to a surface area increased by 33% relative to a surface area of the polymer cores, and an RF value of 1.72 for hybrid microparticles with a closed and hillocky shell structure corresponds to a surface area increased by 72% relative to a surface area of the polymer cores.

8. Method for the synthesis of spherical hybrid microparticles according to claim 1, the method comprises:
preparation of polymer cores by means of a radical polymerization reaction;
coating of the prepared polymer cores with a silicon dioxide layer, using a sol-gel process; and
functionalization of an outer surface of the silicon dioxide layer with an organic chlorosilane or alkoxysilane derivative,
where the preparation of the polymer cores comprises use of the homolytically cleavable initiator 4,4'-azobis(4-cyanopentanoic acid).

9. Method according to claim 8, where
the preparation of the polymer cores takes place in an organic solvent having a water fraction of 0 vol% up to 80 vol% and
comprises the use of styrene as monomer with at least one styrene derivative and/or with at least one comonomer, and further
comprises covalent bonding of a polyvinylpyrrolidone to the surface of the polymer cores, where an average molecular weight of the covalently bonded polyvinylpyrrolidone is selected so that:
the silicon dioxide layer is closed and smooth, and an RF value of the closed and smooth silicon dioxide layer is adjustable in the range from 1 to 1.5; or
the silicon dioxide layer is closed and hillocky and an RF value of the closed and hillocky silicon dioxide layer is adjustable in the range between 1.51 to 3; or
the silicon dioxide layer is open, and an RF value of the open silicon dioxide layer is adjustable to a value of greater than 3.01.

10. Method according to claim 9, where the selected average molecular weight of the polyvinylpyrrolidone
is 10 000 daltons and/or is between 7000 to 11 000 daltons, where the RF value achieved by the closed and smooth silicon dioxide layer is in the range from 1 to 1.5; or
is 11 000 daltons to 58 000 daltons or is between 25 000 daltons and 58 000 daltons, where the RF value achieved by the closed and hillocky silicon dioxide layer is in the range between 1.51 to 3; or
is more than 58 000 daltons, more particularly between 60 000 to 360 000 daltons, where the RF value achieved by the open silicon dioxide layer is above 3.01.

11. Method according to claim 8, where the preparation comprises washing of the polymer cores with an organic or with an aqueous solvent or with a solvent mixture and/or the coating and functionalization takes place in an alcohol/water mixture with an alkoxysilane and/or an organic chlorosilane derivative or an alkoxysilane derivative.

12. Method according to claim 8, where the coating takes place in an alcohol with a water fraction of 0 vol% up to 80 vol%, using a starting substance selected from an alkoxysilane and/or an organic chlorosilane or alkoxysilane derivative in the presence of a basic, an organic or an inorganic catalyst, where the catalyst is selected from ammonia, sodium hydroxide and/or an organic amine.

13. Method according to claim 8, where the functionalization comprises furnishing with amino groups and takes place without an additional catalyst.

14. Method according to claim 8, where the functionalization comprises furnishing with functional groups other than an amino group, and/or takes place using an organic chlorosilane or alkoxysilane derivative with a basic or an acidic catalyst.

15. Method according to claim 9, where the average molecular weight of the polyvinylpyrrolidone is selected from a monodisperse mixture, or a mixture substantially homogeneous in respect of the molecular weight, of PVP molecules of identical molecular weight, or from a heterogeneous mixture comprising PVP molecules having molecular weights which are different from one another.

16. Method according to claim 13, where the microparticles have an amine-modified surface, and the organic chlorosilane or alkoxysilane derivative, at least in sections, forms a closed monolayer or a crosslinked multilayer on the surface.

17. Method according to claim 13, where the amino groups or the other functional groups are bonded covalently on the outer surface of the silicon dioxide layer in each case via an Si-O-Si bond.

18. Method according to claim 8, further comprising:
burning-out of the polymer core at a temperature above 200° C., to leave the silicon dioxide layer as a hollow sphere.

19. Use of 4,4'-azobis(4-cyanopentanoic acid) as initiator for a radical polymerization of styrene, styrene derivatives and/or polystyrene derivatives.

20. Chromatographic support comprising a classified fraction of hybrid microparticles according to claim 1, where the hybrid microparticles are classified according to:
a mean diameter or a range of mean diameters;
a specific surface area or a range of specific surface areas;
an outer structure or a roughness of their outer surface to which an RF value is assigned;
the nature of a functional group present on the outer surface, or the nature of one or more ligands bound thereto.

21. Carrier particles for a particle-based assay, comprising at least one hybrid microparticle according to claim 1, where the at least one hybrid microparticle is characterized by at least one of the parameters set out below:
a mean diameter or a range of mean diameters;
a specific surface area or a range of specific surface areas;
a morphological structure of the outer surface of the shell to which an RF value can be assigned, the RF value being in a range from 1 to 1.5 and the shell being closed and smooth; being in a range of 1.51-3 and the shell being closed and hillocky; or being above 3.01 and the shell being open, where the RF value is defined as the ratio of an external surface area amenable to the adsorption of nitrogen to a surface area which is computable from an arithmetic mean diameter of the hybrid microparticle considered as an ideal sphere;
a density of the hybrid microparticle that is adjustable between a density value of the polymer core which is 1.05 ±0.1 g/ml and the density value of the shell comprising a silicon dioxide layer, which is between 1.8 g/ml to 2.2 g/ml;
a nature of a functional group present on the shell, or the nature of one or more ligands bound thereto or polymer layer;
an analytically analyzable signal which can be captured as a result of a specific interaction between an artificial and/or a biological receptor and/or an analyte-sensitive polymer layer, which are bound on the carrier particle, with the analyte to be detected by the assay, where the analytically analyzable signal comprises a fluorescence property.

* * * * *